United States Patent
Bierman

(10) Patent No.: US 10,569,059 B2
(45) Date of Patent: Feb. 25, 2020

(54) GUIDEWIRE RETENTION DEVICE

(71) Applicant: Access Scientific, LLC, San Diego, CA (US)

(72) Inventor: Steven F. Bierman, Del Mar, CA (US)

(73) Assignee: ASSPV, LLC, San Diego, CA (US)

( * ) Notice: Subject to any disclaimer, the term of this patent is extended or adjusted under 35 U.S.C. 154(b) by 0 days.

(21) Appl. No.: 15/942,217

(22) Filed: Mar. 30, 2018

(65) Prior Publication Data

US 2019/0269890 A1   Sep. 5, 2019

Related U.S. Application Data

(60) Provisional application No. 62/648,522, filed on Mar. 27, 2018, provisional application No. 62/637,317, filed on Mar. 1, 2018.

(51) Int. Cl.
| | |
|---|---|
| *A61M 25/00* | (2006.01) |
| *A61M 25/09* | (2006.01) |
| *A61M 29/00* | (2006.01) |
| *A61M 25/06* | (2006.01) |

(52) U.S. Cl.
CPC ........ *A61M 25/09* (2013.01); *A61M 25/0606* (2013.01); *A61M 25/0668* (2013.01); *A61M 25/09041* (2013.01); *A61M 29/00* (2013.01); *A61M 25/0662* (2013.01); *A61M 2025/0681* (2013.01); *A61M 2025/0687* (2013.01); *A61M 2025/09125* (2013.01)

(58) Field of Classification Search
CPC .............. A61M 39/06; A61M 39/0606; A61M 39/0613; A61M 2039/062; A61M 203/0633; A61M 2039/066; A61M 2039/0673; A61M 2039/068; A61M 2039/0686; A61M 39/0693; A61M 2039/0633
See application file for complete search history.

(56) References Cited

U.S. PATENT DOCUMENTS

| | | |
|---|---|---|
| 500,740 A | 7/1893 | Doyle |
| 1,436,882 A | 11/1922 | Knepper |
| 3,185,152 A | 5/1965 | Ring |
| 3,539,034 A | 11/1970 | Tafeen |
| 3,540,447 A | 11/1970 | Howe et al. |
| 3,565,074 A | 2/1971 | Foti et al. |
| 3,670,729 A | 6/1972 | Bennett et al. |
| 3,680,562 A | 8/1972 | Wittes |

(Continued)

FOREIGN PATENT DOCUMENTS

| | | |
|---|---|---|
| DE | 2052364 | 4/1972 |
| DE | 8915299 | 2/1990 |

(Continued)

OTHER PUBLICATIONS

Arrow Trauma Products No. TRM-C 12/00 11M, Arrow International, 2000.

(Continued)

*Primary Examiner* — William R Carpenter
(74) *Attorney, Agent, or Firm* — Knobbe Martens Olson & Bear, LLP

(57) ABSTRACT

The device includes a dilator having a locking mechanism configured to limit a distance a guidewire can be advanced out of a distal end of the dilator.

30 Claims, 24 Drawing Sheets

(56) References Cited

U.S. PATENT DOCUMENTS

| | | |
|---|---|---|
| 3,993,079 A | 11/1976 | Gatztanondo |
| 3,995,628 A | 12/1976 | Gula et al. |
| 4,068,659 A | 1/1978 | Moorehead |
| 4,068,660 A | 1/1978 | Beck |
| 4,072,146 A | 2/1978 | Howes |
| 4,170,993 A | 10/1979 | Alvarez |
| 4,191,186 A | 3/1980 | Keeler |
| 4,192,305 A | 3/1980 | Seberg |
| 4,205,675 A | 6/1980 | Vaillancourt |
| 4,230,109 A | 10/1980 | Geiss |
| 4,230,123 A | 10/1980 | Hawkins, Jr. |
| 4,233,974 A | 11/1980 | Desecki et al. |
| 4,274,408 A | 6/1981 | Nimrod |
| 4,333,505 A | 6/1982 | Jones et al. |
| 4,345,596 A | 8/1982 | Young |
| 4,411,655 A | 10/1983 | Schreck |
| 4,412,832 A | 11/1983 | Kling et al. |
| 4,417,886 A | 11/1983 | Frankhouser et al. |
| 4,445,893 A | 5/1984 | Bodicky |
| 4,512,351 A | 4/1985 | Pohndorf |
| 4,525,157 A | 6/1985 | Vaillancourt |
| 4,539,003 A | 9/1985 | Tucker |
| 4,581,019 A | 4/1986 | Curelaru et al. |
| 4,610,665 A | 9/1986 | Matsumoto et al. |
| 4,629,450 A | 12/1986 | Susuki et al. |
| 4,652,256 A | 3/1987 | Vaillancourt |
| 4,655,750 A | 4/1987 | Vaillancourt |
| 4,661,300 A | 4/1987 | Daugherty |
| 4,752,292 A | 6/1988 | Lopez et al. |
| 4,772,264 A | 9/1988 | Cragg |
| 4,791,937 A | 12/1988 | Wang |
| 4,826,486 A | 5/1989 | Palsrok et al. |
| 4,850,960 A | 7/1989 | Grayzel |
| 4,850,975 A | 7/1989 | Furukawa |
| 4,869,259 A | 9/1989 | Elkins |
| 4,894,052 A | 1/1990 | Crawford |
| 4,917,669 A | 4/1990 | Bonaldo |
| 4,917,679 A | 4/1990 | Kronner |
| 4,944,728 A | 7/1990 | Carrell |
| 4,950,252 A | 8/1990 | Luther et al. |
| 4,952,207 A | 8/1990 | Lemieux |
| 4,955,890 A | 9/1990 | Yamamoto et al. |
| 4,961,729 A | 10/1990 | Vaillancourt |
| 4,978,334 A | 12/1990 | Toye et al. |
| 4,995,866 A | 2/1991 | Amplatz et al. |
| 4,997,421 A | 3/1991 | Palsrok et al. |
| 5,045,065 A | 9/1991 | Raulerson |
| 5,049,136 A | 9/1991 | Johnson |
| 5,053,017 A | 10/1991 | Chamuel |
| 5,059,186 A | 10/1991 | Yamamoto et al. |
| 5,064,414 A | 11/1991 | Revane |
| 5,066,284 A | 11/1991 | Mersch et al. |
| 5,067,945 A | 11/1991 | Ryan et al. |
| 5,098,389 A | 3/1992 | Cappucci |
| 5,098,392 A | 3/1992 | Fleischhacker et al. |
| 5,102,394 A | 4/1992 | Lasaitis et al. |
| 5,105,807 A | 4/1992 | Kahn et al. |
| 5,108,374 A | 4/1992 | Lemieux |
| 5,112,308 A | 5/1992 | Olsen et al. |
| 5,114,401 A | 5/1992 | Stuart et al. |
| 5,135,502 A | 8/1992 | Koenig, Jr. et al. |
| 5,135,505 A | 8/1992 | Kaufman |
| 5,158,544 A | 10/1992 | Weinstein |
| 5,167,637 A | 12/1992 | Okada et al. |
| 5,171,218 A | 12/1992 | Fonger et al. |
| 5,215,525 A | 6/1993 | Sturman |
| 5,215,528 A | 6/1993 | Purdy et al. |
| 5,242,410 A | 9/1993 | Melker |
| 5,242,414 A | 9/1993 | Fischell et al. |
| 5,242,427 A | 9/1993 | Bilweis |
| 5,246,426 A | 9/1993 | Lewis et al. |
| 5,248,306 A | 9/1993 | Clark et al. |
| 5,250,038 A | 10/1993 | Melker et al. |
| 5,255,691 A | 10/1993 | Otten |
| 5,279,590 A | 1/1994 | Sinko et al. |
| 5,295,969 A | 3/1994 | Fischell |
| 5,295,970 A | 3/1994 | Clinton et al. |
| 5,306,253 A | 4/1994 | Brimhall |
| 5,312,355 A | 5/1994 | Lee |
| 5,312,359 A | 5/1994 | Wallace |
| 5,314,411 A | 5/1994 | Bierman et al. |
| 5,328,480 A | 7/1994 | Melker et al. |
| 5,330,433 A | 7/1994 | Fonger et al. |
| 5,334,149 A | 8/1994 | Nortman et al. |
| 5,334,157 A | 8/1994 | Klein et al. |
| 5,336,191 A | 8/1994 | Davis et al. |
| 5,342,315 A | 8/1994 | Rowe et al. |
| 5,366,441 A | 11/1994 | Crawford |
| 5,380,290 A | 1/1995 | Makower et al. |
| 5,388,589 A | 2/1995 | Davis |
| 5,391,152 A | 2/1995 | Patterson |
| 5,391,178 A | 2/1995 | Yapor |
| 5,397,311 A | 3/1995 | Walker et al. |
| 5,403,283 A | 4/1995 | Luther |
| 5,419,766 A | 5/1995 | Chang et al. |
| 5,425,718 A | 6/1995 | Tay et al. |
| 5,468,024 A | 11/1995 | Carman et al. |
| 5,512,052 A * | 4/1996 | Jesch ............. A61B 17/3415 604/158 |
| 5,520,654 A | 5/1996 | Wahlberg |
| 5,531,701 A | 7/1996 | Luther |
| 5,531,713 A | 7/1996 | Mastronardi et al. |
| 5,542,932 A | 8/1996 | Daugherty |
| 5,589,120 A | 12/1996 | Khan et al. |
| 5,676,653 A | 10/1997 | Taylor et al. |
| 5,676,658 A | 10/1997 | Erskine |
| 5,676,689 A | 10/1997 | Kensey et al. |
| 5,685,856 A | 11/1997 | Lehrer |
| 5,688,249 A | 11/1997 | Chang et al. |
| 5,688,570 A | 11/1997 | Ruttinger |
| 5,690,619 A | 11/1997 | Erskine |
| 5,704,914 A | 1/1998 | Stocking et al. |
| 5,712,229 A | 1/1998 | Hopkins et al. |
| 5,713,876 A | 2/1998 | Bogert |
| 5,728,132 A | 3/1998 | Van Tassel et al. |
| 5,749,857 A | 5/1998 | Cuppy |
| 5,795,339 A | 8/1998 | Erskine |
| 5,810,780 A | 9/1998 | Brimhall et al. |
| 5,820,596 A | 10/1998 | Rosen et al. |
| 5,827,202 A | 10/1998 | Miraki et al. |
| 5,830,190 A | 11/1998 | Howell |
| 5,833,662 A | 11/1998 | Stevens |
| 5,853,393 A | 12/1998 | Bogert |
| 5,858,002 A | 1/1999 | Jesch |
| 5,865,806 A | 2/1999 | Howell |
| 5,885,217 A | 3/1999 | Gisselberg et al. |
| 5,885,253 A | 3/1999 | Liu |
| 5,902,254 A | 5/1999 | Magram |
| 5,904,657 A | 5/1999 | Unsworth et al. |
| 5,910,132 A | 6/1999 | Schultz |
| 5,919,160 A | 7/1999 | Sanfilippo |
| 5,935,110 A | 8/1999 | Brimhall |
| 5,954,708 A | 9/1999 | Lopez et al. |
| 5,957,894 A | 9/1999 | Kerwin et al. |
| 5,984,895 A | 11/1999 | Padilla et al. |
| 6,004,294 A | 12/1999 | Brimhall et al. |
| 6,027,480 A | 2/2000 | Davis et al. |
| 6,046,143 A | 4/2000 | Khan et al. |
| 6,074,377 A | 6/2000 | Sanfilippo |
| 6,080,141 A | 6/2000 | Castro et al. |
| 6,117,108 A * | 9/2000 | Woehr ............. A61M 25/0618 604/110 |
| 6,117,140 A * | 9/2000 | Munsinger ............. A61F 2/95 606/108 |
| 6,120,494 A | 9/2000 | Jonkman |
| 6,137,468 A | 10/2000 | Martinez et al. |
| 6,156,010 A | 12/2000 | Kuracina et al. |
| 6,159,179 A | 12/2000 | Simonson |
| 6,179,813 B1 | 1/2001 | Ballow et al. |
| 6,210,366 B1 | 4/2001 | Sanfilippo |
| 6,245,044 B1 | 6/2001 | Daw et al. |
| 6,273,871 B1 | 8/2001 | Davis et al. |
| 6,277,100 B1 | 8/2001 | Raulerson |
| 6,287,278 B1 | 9/2001 | Woehr et al. |

(56) References Cited

U.S. PATENT DOCUMENTS

| | | |
|---|---|---|
| 6,287,322 B1 | 9/2001 | Zhu et al. |
| 6,328,717 B1 | 12/2001 | Solomon et al. |
| 6,336,914 B1 | 1/2002 | Gillespie, III |
| 6,379,333 B1 | 4/2002 | Brimhall et al. |
| 6,436,070 B1 | 8/2002 | Botich et al. |
| 6,461,362 B1 | 10/2002 | Halseth et al. |
| 6,475,207 B1 | 11/2002 | Maginot |
| 6,488,662 B2 | 12/2002 | Sirimanne |
| 6,500,152 B1 | 12/2002 | Illi |
| 6,524,277 B1 | 2/2003 | Chang |
| 6,567,101 B1 | 5/2003 | Thomas |
| 6,602,240 B2 * | 8/2003 | Hermann ............ A61B 17/3462 251/4 |
| 6,607,353 B2 | 8/2003 | Masutani |
| 6,607,511 B2 | 8/2003 | Halseth et al. |
| 6,626,868 B1 | 9/2003 | Prestidge et al. |
| 6,641,564 B1 | 11/2003 | Kraus |
| 6,692,462 B2 | 2/2004 | Mackenzie et al. |
| 6,692,482 B2 | 2/2004 | Heller et al. |
| 6,695,816 B2 | 2/2004 | Cassidy |
| 6,714,809 B2 | 3/2004 | Lee et al. |
| 6,719,772 B2 | 4/2004 | Trask et al. |
| 6,726,659 B1 | 4/2004 | Stocking et al. |
| 6,749,588 B1 | 6/2004 | Howell et al. |
| 6,786,875 B2 | 9/2004 | Barker et al. |
| 6,808,520 B1 | 10/2004 | Fourkas |
| 6,836,687 B2 | 12/2004 | Kelley |
| 6,905,481 B2 | 6/2005 | Sirimanne |
| 6,940,092 B2 | 9/2005 | Yoshida et al. |
| 6,972,002 B2 | 12/2005 | Thorne |
| 6,994,693 B2 | 2/2006 | Tal |
| 7,001,396 B2 | 2/2006 | Glazier et al. |
| 7,025,746 B2 | 4/2006 | Tal |
| 7,109,967 B2 | 9/2006 | Hioki et al. |
| 7,182,755 B2 | 2/2007 | Tal |
| 7,192,433 B2 | 3/2007 | Osypka et al. |
| 7,196,689 B2 | 3/2007 | Moriyama |
| 7,226,434 B2 | 6/2007 | Carlyon et al. |
| 7,270,649 B2 | 9/2007 | Fitzgerald |
| 7,455,660 B2 | 11/2008 | Schweikert et al. |
| 7,458,954 B2 * | 12/2008 | Ferguson ............ A61M 25/0618 604/110 |
| 7,500,965 B2 | 3/2009 | Menzi et al. |
| 7,503,596 B2 | 3/2009 | Rome et al. |
| 7,556,617 B2 | 7/2009 | Voorhees, Jr. et al. |
| 7,614,123 B2 | 11/2009 | Schweikert |
| 7,670,316 B2 | 3/2010 | Windhueser et al. |
| 7,682,339 B2 | 3/2010 | Fujii |
| 7,722,567 B2 | 5/2010 | Tal |
| 7,827,656 B2 | 11/2010 | Schweikert |
| 7,833,202 B2 | 11/2010 | Suzuki |
| 7,922,696 B2 | 4/2011 | Tal et al. |
| 8,021,338 B2 | 9/2011 | Adams |
| 8,070,750 B2 | 12/2011 | Wenstrom, Jr. et al. |
| 8,105,286 B2 | 1/2012 | Anderson et al. |
| 8,192,402 B2 | 6/2012 | Anderson et al. |
| 8,202,251 B2 | 6/2012 | Bierman et al. |
| 8,211,087 B2 | 7/2012 | Carter et al. |
| 8,377,006 B2 | 2/2013 | Tal et al. |
| 8,545,533 B2 | 10/2013 | Spenser et al. |
| 8,628,497 B2 | 1/2014 | Finnestad et al. |
| 8,657,790 B2 | 2/2014 | Tal et al. |
| 8,672,888 B2 | 3/2014 | Tal |
| 8,900,192 B2 | 12/2014 | Anderson et al. |
| 8,915,884 B2 | 12/2014 | Tal et al. |
| 8,956,327 B2 | 2/2015 | Bierman et al. |
| 9,375,553 B2 | 6/2016 | Chrisman |
| 9,402,979 B2 * | 8/2016 | Alokaili ............ A61M 25/09041 |
| 9,764,117 B2 | 9/2017 | Bierman et al. |
| 10,136,916 B2 | 11/2018 | Bierman et al. |
| 2002/0010436 A1 | 1/2002 | Becker et al. |
| 2002/0072712 A1 | 6/2002 | Nool et al. |
| 2002/0087076 A1 | 7/2002 | Meguro et al. |
| 2003/0032927 A1 | 2/2003 | Halseth et al. |
| 2003/0060842 A1 | 3/2003 | Chin et al. |
| 2003/0171718 A1 | 9/2003 | Delegge |
| 2003/0199827 A1 | 10/2003 | Thorne |
| 2003/0216771 A1 | 11/2003 | Osypka et al. |
| 2004/0008191 A1 | 1/2004 | Poupyrev et al. |
| 2004/0092879 A1 | 5/2004 | Kraus et al. |
| 2004/0102789 A1 | 5/2004 | Baughman |
| 2004/0167439 A1 * | 8/2004 | Sharrow ............ A61M 25/09 600/585 |
| 2004/0171988 A1 | 9/2004 | Moretti |
| 2004/0193112 A1 | 9/2004 | Glazier et al. |
| 2004/0199197 A1 * | 10/2004 | Eidenschink ...... A61M 25/0113 606/194 |
| 2004/0239687 A1 | 12/2004 | Idesawa et al. |
| 2005/0027263 A1 | 2/2005 | Woehr et al. |
| 2005/0113798 A1 | 5/2005 | Slater et al. |
| 2005/0143770 A1 | 6/2005 | Carter et al. |
| 2005/0245875 A1 | 11/2005 | Restelli et al. |
| 2006/0015071 A1 | 1/2006 | Fitzgerald |
| 2006/0274036 A1 | 12/2006 | Hoiki et al. |
| 2007/0021685 A1 | 1/2007 | Oepen et al. |
| 2007/0060889 A1 | 3/2007 | Adams |
| 2007/0161908 A1 | 7/2007 | Goldman et al. |
| 2007/0270751 A1 | 11/2007 | Stangenes et al. |
| 2007/0282300 A1 | 12/2007 | Attawia et al. |
| 2008/0262430 A1 * | 10/2008 | Anderson .......... A61B 17/3415 604/164.1 |
| 2009/0149857 A1 | 6/2009 | Culbert et al. |
| 2009/0163861 A1 | 6/2009 | Carlyon |
| 2009/0221961 A1 | 9/2009 | Tal et al. |
| 2009/0264867 A1 | 10/2009 | Schweikert et al. |
| 2010/0069880 A1 | 3/2010 | Grayzel et al. |
| 2010/0191189 A1 | 7/2010 | Harding et al. |
| 2010/0256567 A1 | 10/2010 | Smith |
| 2011/0021994 A1 | 1/2011 | Anderson et al. |
| 2011/0046564 A1 | 2/2011 | Zhong |
| 2011/0202006 A1 | 8/2011 | Bierman et al. |
| 2011/0218496 A1 | 9/2011 | Bierman |
| 2011/0276002 A1 | 11/2011 | Bierman |
| 2012/0004665 A1 * | 1/2012 | Defossez .......... A61B 17/8872 606/108 |
| 2012/0130307 A1 | 5/2012 | Pobitschka |
| 2012/0283640 A1 | 11/2012 | Anderson et al. |
| 2014/0025036 A1 | 1/2014 | Bierman et al. |
| 2014/0081210 A1 | 3/2014 | Bierman et al. |
| 2015/0297868 A1 | 10/2015 | Tal et al. |
| 2015/0351793 A1 | 12/2015 | Bierman et al. |
| 2017/0291009 A1 | 10/2017 | Sos |
| 2018/0001060 A1 | 1/2018 | Bierman et al. |
| 2018/0296804 A1 | 10/2018 | Bierman |
| 2019/0076166 A1 | 3/2019 | Bierman |

FOREIGN PATENT DOCUMENTS

| | | |
|---|---|---|
| DE | 8914941 | 9/1990 |
| DE | 20211804 | 1/2003 |
| EP | 0129745 | 1/1985 |
| EP | 0139091 | 5/1985 |
| EP | 0352928 | 1/1990 |
| EP | 0411605 | 2/1991 |
| EP | 0583144 | 2/1994 |
| EP | 0502714 | 11/1995 |
| EP | 0745409 | 12/1996 |
| EP | 0750916 | 1/1997 |
| EP | 1570793 | 9/2005 |
| FR | 2 368 968 | 5/1978 |
| JP | 53-51692 | 5/1978 |
| JP | 06-285172 | 10/1994 |
| JP | 07-148270 | 6/1995 |
| JP | 08-336593 | 12/1996 |
| JP | 11-299897 | 11/1999 |
| JP | 2001-190682 | 7/2001 |
| JP | 2003-512903 | 4/2003 |
| JP | 2003-154013 | 5/2003 |
| JP | 2004-500218 | 1/2004 |
| JP | 2004-097843 | 4/2004 |
| JP | 2005-514114 | 5/2005 |
| JP | 2007-503172 | 2/2007 |
| JP | 2007-209721 | 8/2007 |

(56) References Cited

FOREIGN PATENT DOCUMENTS

| | | |
|---|---|---|
| JP | 2010-504295 | 2/2010 |
| JP | 2016-163667 | 9/2016 |
| KR | 10-2005-0027359 | 3/2005 |
| WO | WO 83/01575 | 5/1983 |
| WO | WO 88/07388 | 10/1988 |
| WO | WO 92/18193 | 10/1992 |
| WO | WO 93/11812 | 6/1993 |
| WO | WO 93/12826 | 7/1993 |
| WO | WO 94/12233 | 6/1994 |
| WO | WO 98/04189 | 2/1998 |
| WO | WO 98/024494 | 6/1998 |
| WO | WO 98/57685 | 12/1998 |
| WO | WO 00/00104 | 1/2000 |
| WO | WO 01/23028 | 4/2001 |
| WO | WO 01/024865 | 4/2001 |
| WO | WO 01/041860 | 6/2001 |
| WO | WO 01/78595 | 10/2001 |
| WO | WO 03/057272 | 7/2003 |
| WO | WO 06/119503 | 11/2006 |
| WO | WO 08/064332 | 5/2008 |
| WO | WO 13/067518 | 5/2013 |

OTHER PUBLICATIONS

Photograph of various access devices.
Photos of a peripheral emergency infusion device Applicant believes to be produced by Arrow International Inc., Jul. 20, 2011.
Photos of a splittable catheter design, Jul. 20, 2011.
Photos of an infusion device Applicant believes to be produced by B. Braun Medical Inc., Jul. 20, 2011.
U.S. Department of Health and Human Resources, "Medical Devices with Sharps Injury Prevention Features," Guidance for Industry and FDA Staff in 20 pages. Issued on Aug. 9, 2005.
International Search Report and Written Opinion in Application No. PCT/US2019/019640 dated Jun. 5, 2019 31 pages.

* cited by examiner

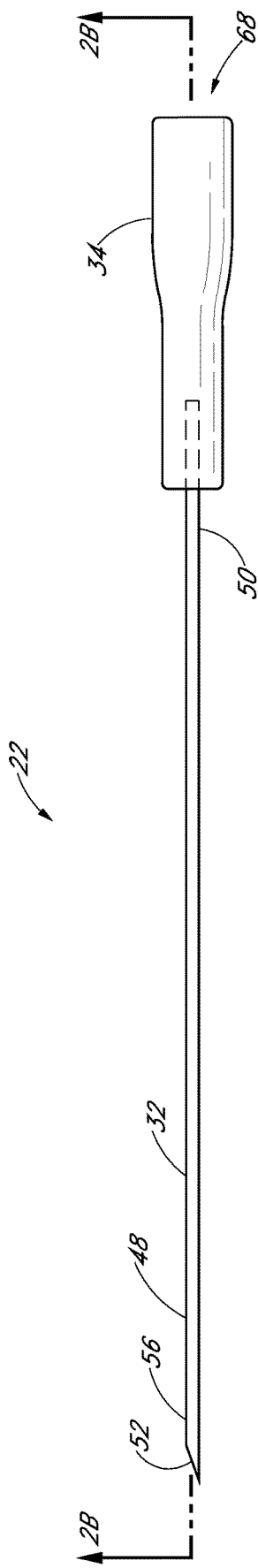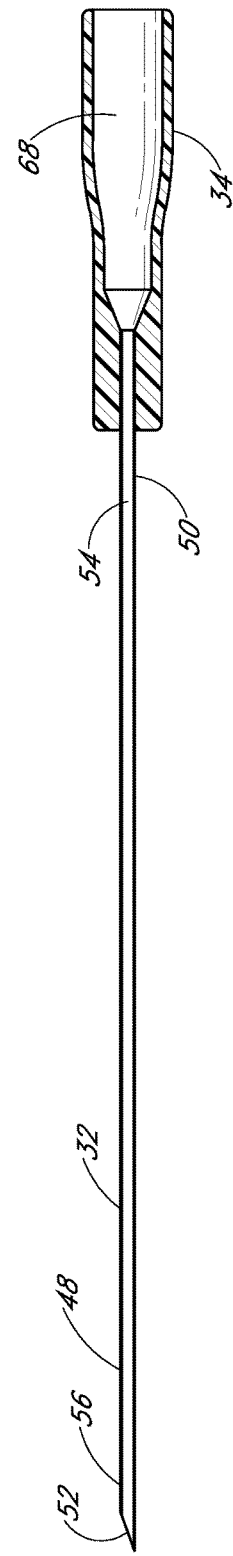
FIG. 2A
FIG. 2B

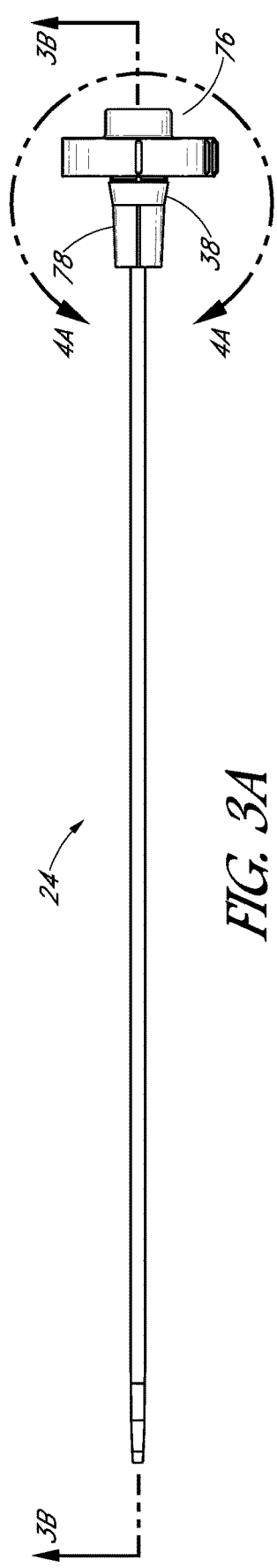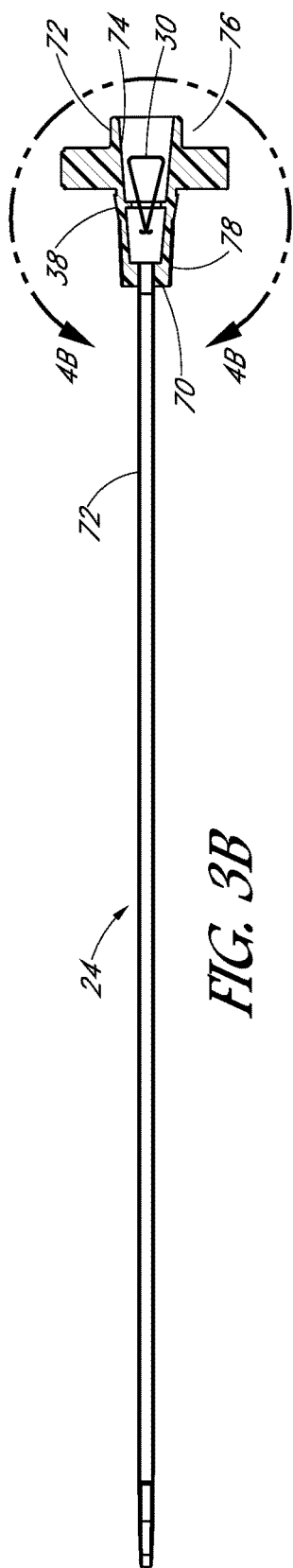
FIG. 3A
FIG. 3B

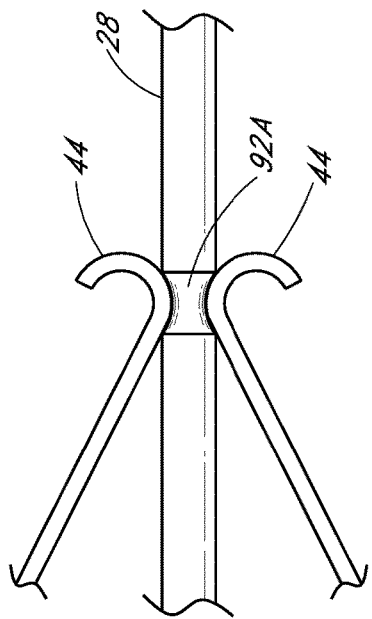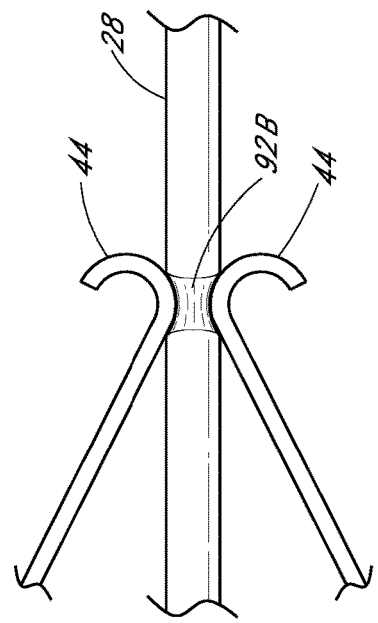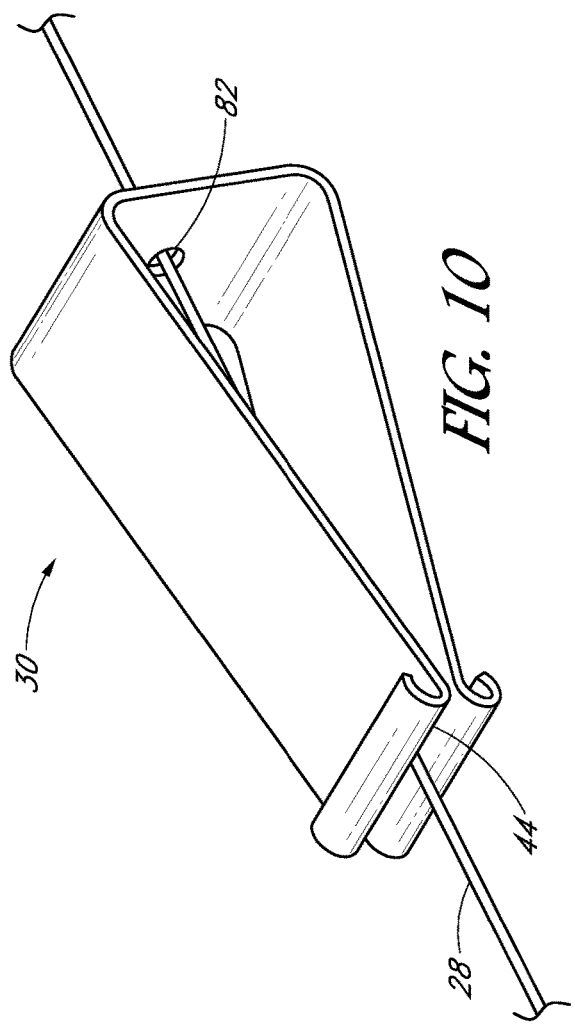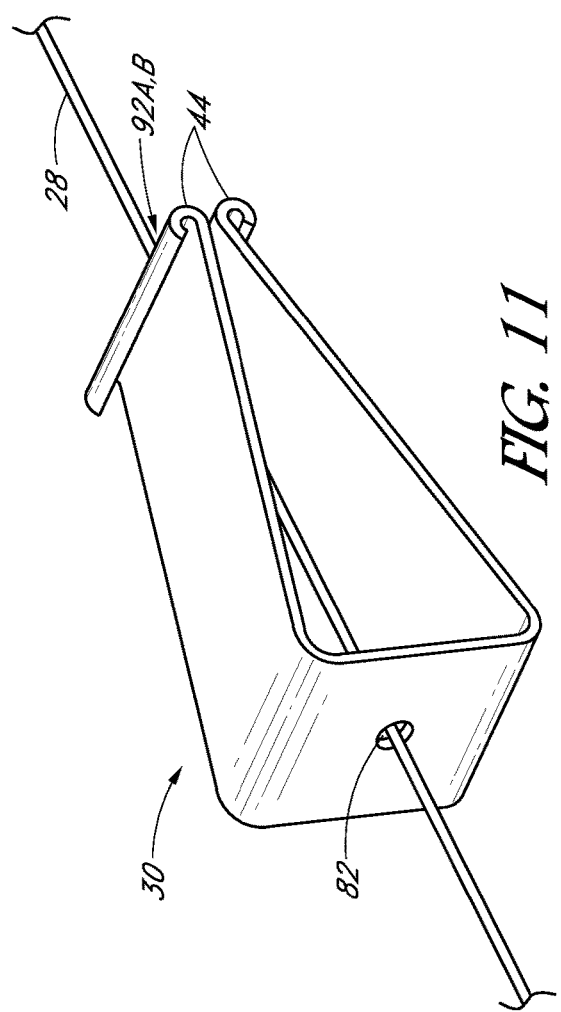

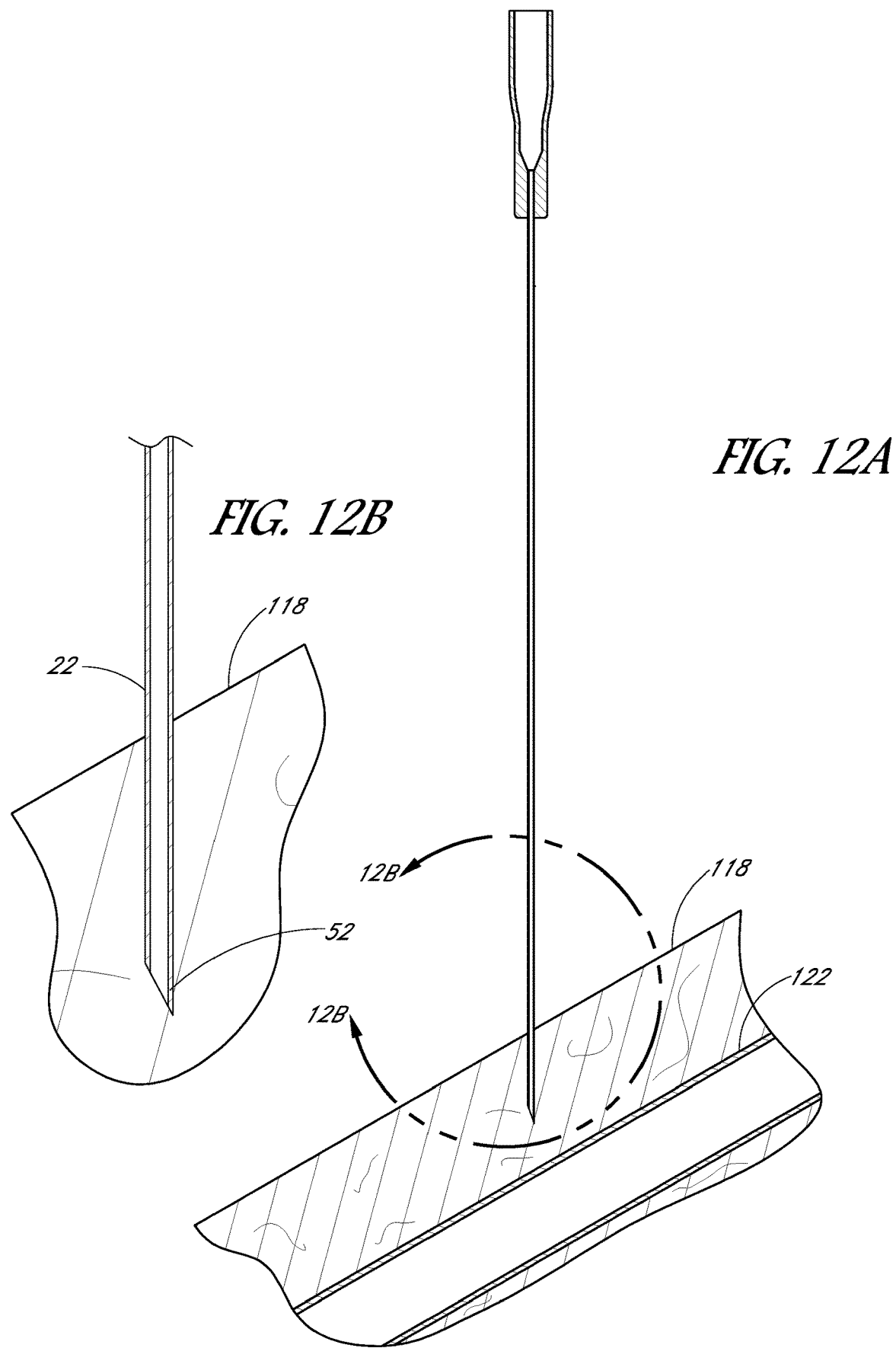

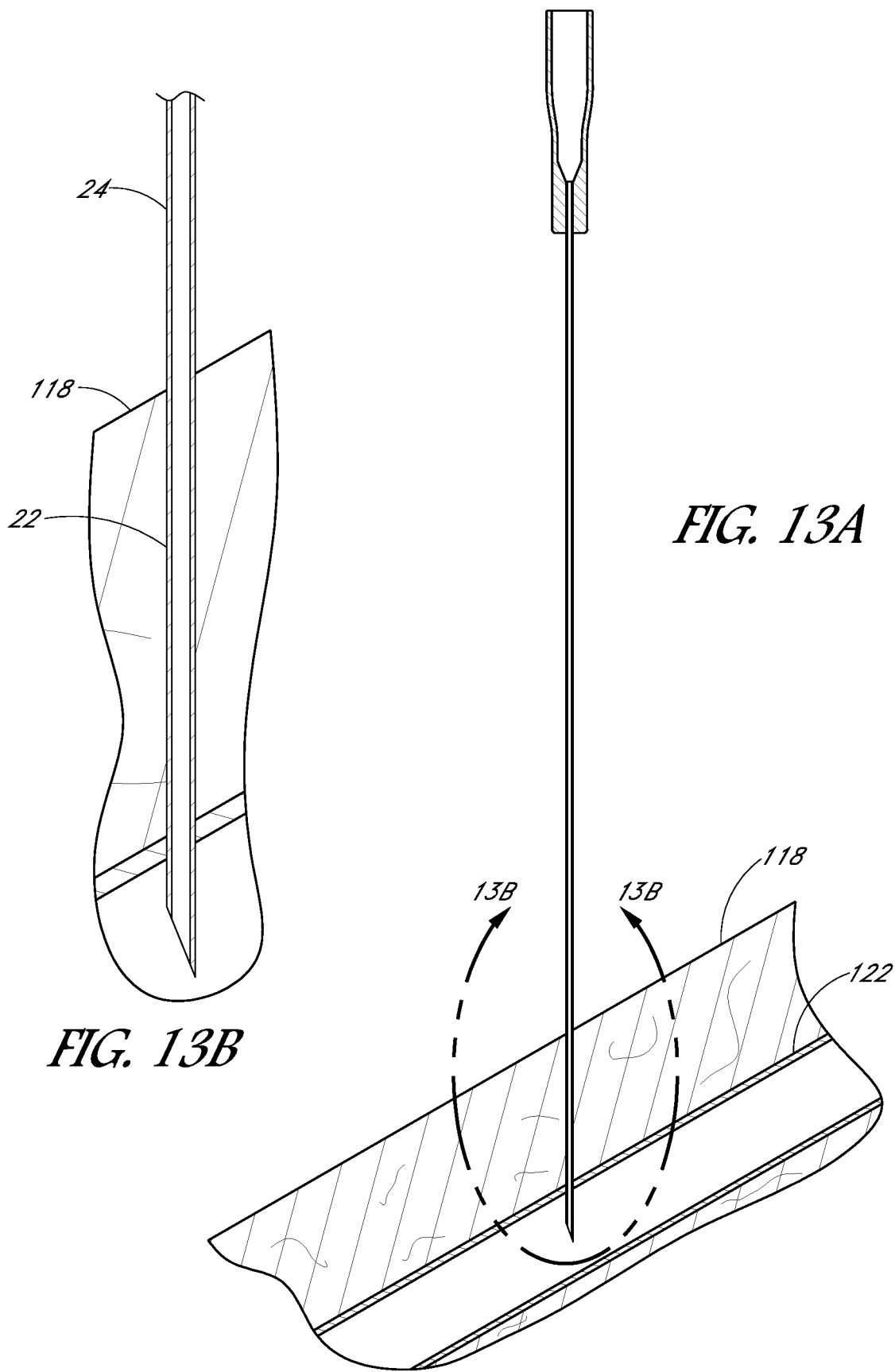

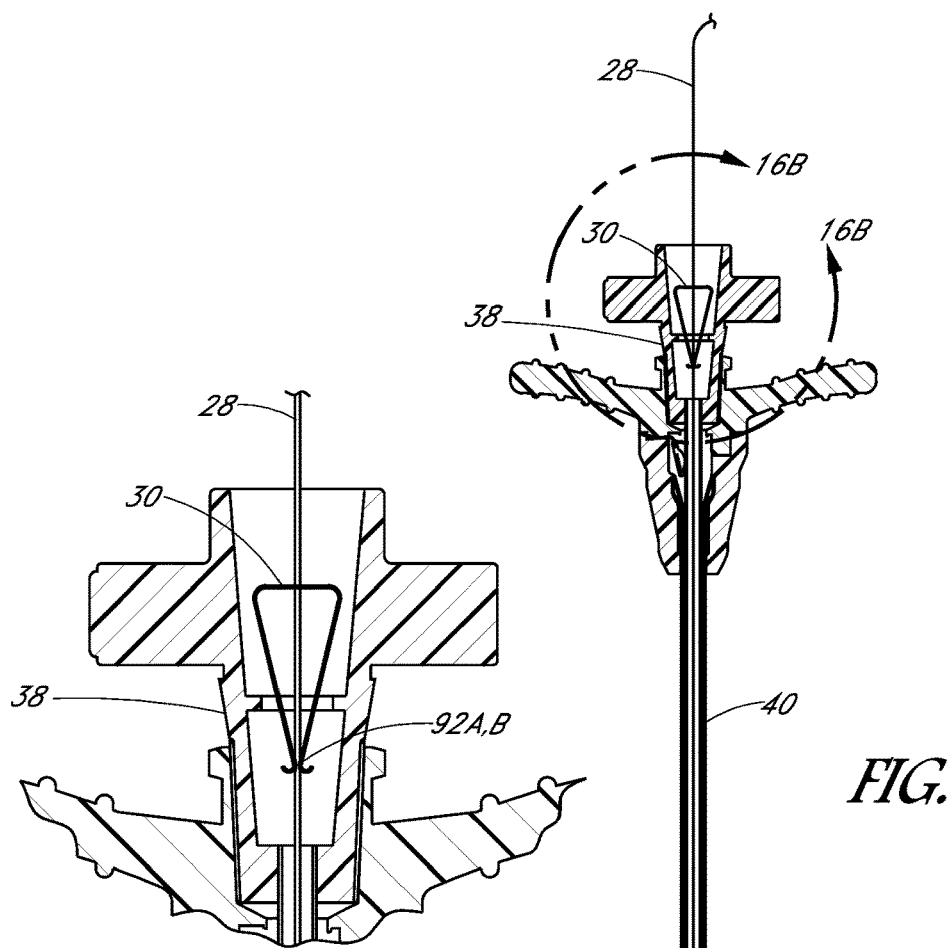
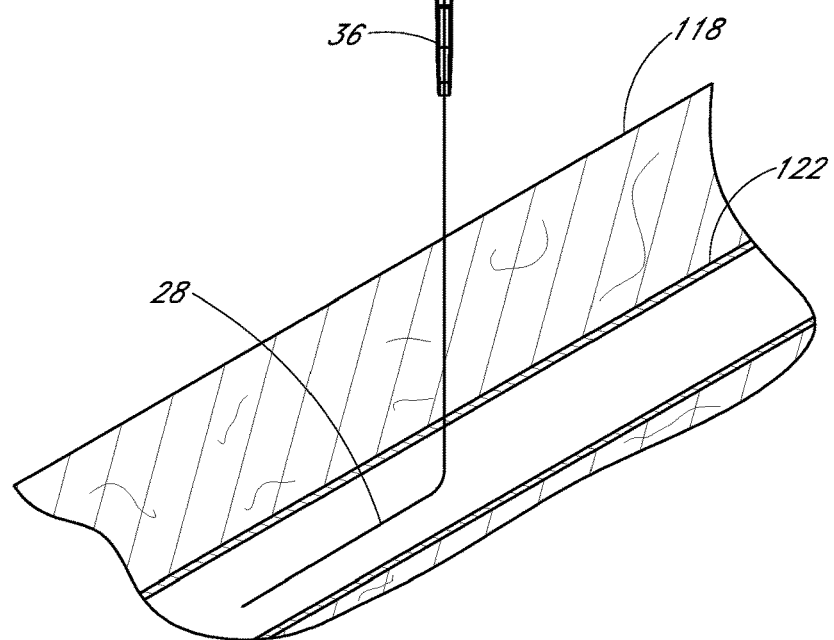
FIG. 16A
FIG. 16B

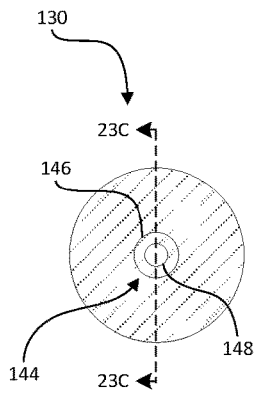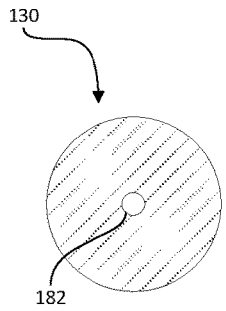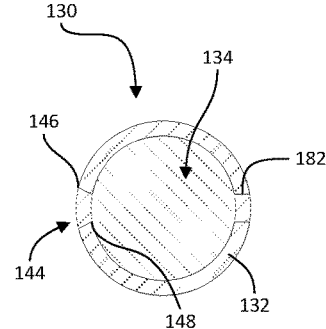
FIG. 23A  FIG. 23B  FIG. 23C
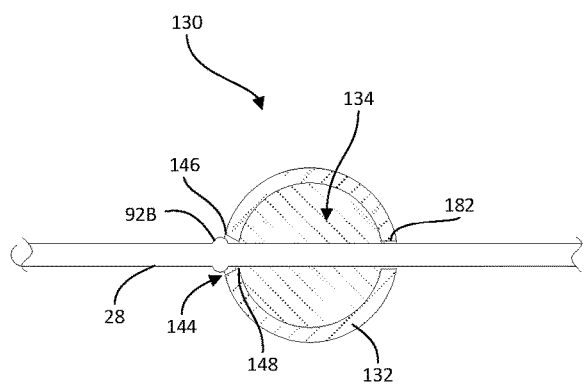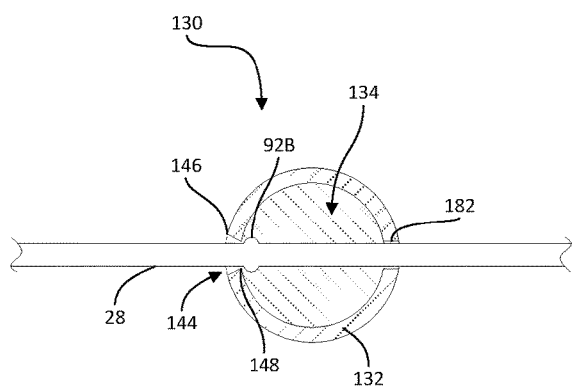
FIG. 24A  FIG. 24B

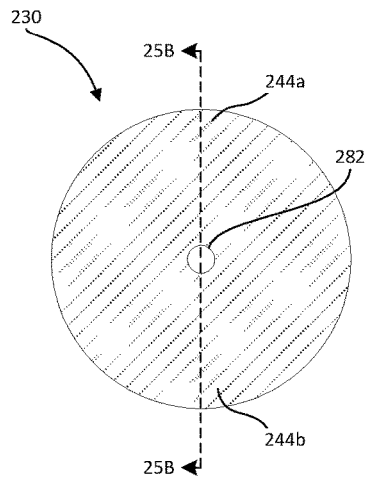
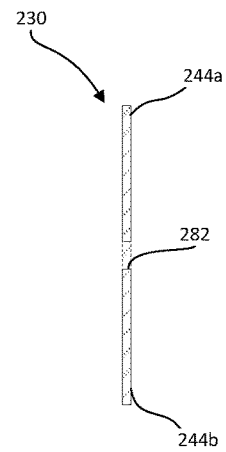
FIG. 25A  FIG. 25B
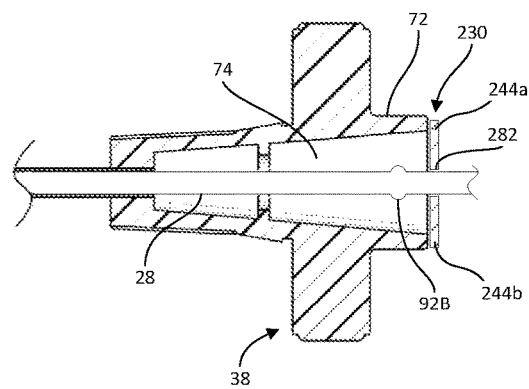
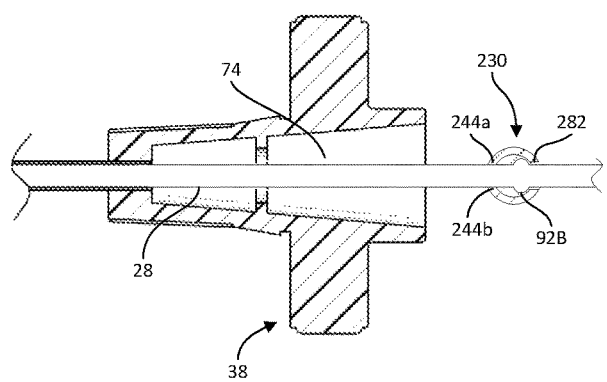
FIG. 26A  FIG. 26B

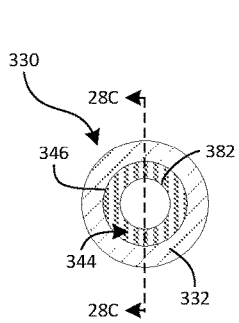 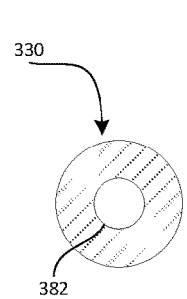 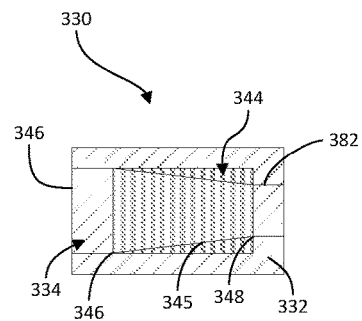
FIG. 28A  FIG. 28B  FIG. 28C
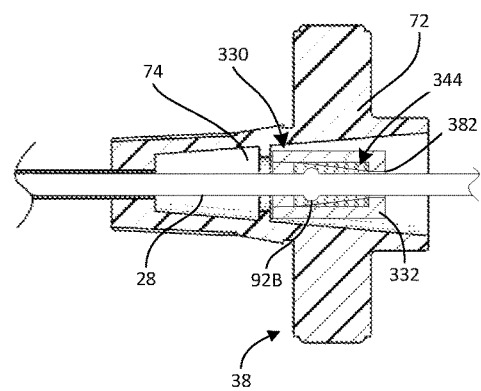 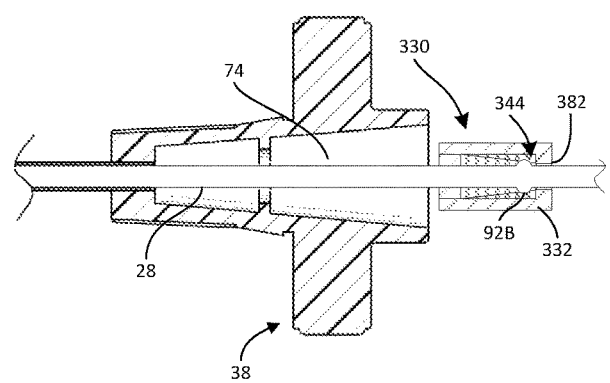
FIG. 29A  FIG. 29B

GUIDEWIRE RETENTION DEVICE

INCORPORATION BY REFERENCE

The entire contents of U.S. Provisional Patent Application No. 62/637,317, filed on Mar. 1, 2018, and U.S. Provisional Patent Application No. 62/648,522, filed on Mar. 27, 2018, are hereby incorporated by reference herein in their entireties, forming part of the present disclosure. Any feature, structure, material, method, or step that is described and/or illustrated in any embodiment in the foregoing provisional patent application can be used with or instead of any feature, structure, material, method, or step that is described in the following paragraphs of this specification and/or illustrated in the accompanying drawings.

BACKGROUND

Field of the Invention

The present disclosure is generally directed to access devices for introducing and/or delivering a medical article (such as, for example, a catheter, cannula, sheath, etc.) into a body space, such as, for example, an artery, vein, vessel, body cavity, or drainage site, and more specifically, to devices which include structure for interlocking or engaging with a guidewire.

Description of the Related Art

A preferred non-surgical method for inserting a catheter or vascular sheath into a blood vessel involves the use of the Seldinger or a modified Seldinger technique, which includes an access needle that is inserted into a patient's blood vessel. A guidewire is inserted through the needle and into the vessel. The needle is removed, and a dilator and sheath in combination or separately are then inserted over the guidewire. The dilator and sheath, together or separately, are then inserted a short distance through the tissue into the vessel, after which the dilator and guidewire are removed and discarded. A catheter or other medical article may then be inserted through the sheath into the vessel to a desired location, or the sheath may simply be left in the vessel.

The above technique requires exchanges over the guidewire, which presents the risk of losing cannulation, lost guidewire, and contamination. The overall technique is time intensive risking movement of the medical article(s) and guidewire relative to the patient. Thus, there exists a need for an easier-to-use and safer vascular access device, especially one that would reduce accidental embolization and other attendant risks of over-wire vascular access.

SUMMARY

The access devices described herein advantageously provide improved mechanisms for safely achieving medical device placement within the vasculature. Without limiting the scope of this disclosure, its more prominent features will be discussed briefly. After considering this discussion, and particularly after reading the Detailed Description of the Preferred Embodiments section below in combination with this section, one will understand how the features and aspects of these embodiments provide several advantages over prior access devices.

One aspect is an access device for placing a medical article within a body space. The access device includes a dilator having a hub and an elongated dilator body extending from the hub. The access device further includes a guidewire configured to slide within the dilator body and having a guidewire stop. The access device further includes a locking mechanism supported by the dilator and having a guidewire lock. The locking mechanism being configured to interlock with the guidewire at least when the dilator is threaded over the guidewire and the guidewire lock axially aligns with the guidewire stop.

Another aspect is an access device for placing a medical article within a body space. The access device includes a guidewire having a guidewire stop and a dilator configured to be coaxially disposed about the guidewire. The access device further includes a locking mechanism disposed on the dilator and configured to move from an unlocked state to a locked state. The locking mechanism is disengaged from the guidewire when the locking mechanism is in the unlocked state so as to allow axial movement by the guidewire through the locking mechanism in a proximal direction and a distal direction. The locking mechanism is engaged with the guidewire when the locking mechanism is in the locked state so as to limit at least axial movement of a portion of the guidewire in the distal direction relative to at least a portion of the dilator.

Yet another aspect is a method of limiting a distance a guidewire can be advanced out of a distal end of a dilator and into a patient's body. The method includes puncturing a patient's body with a needle having an interior bore, sliding a guidewire through the interior bore and into the patient's body, and removing the needle from the patient's body. The method further comprises threading a dilator over the guidewire and into the patient's body. The dilator includes a locking mechanism configured to receive the guidewire and interlock to the guidewire so as to inhibit at least relative axial movement between at least a portion of the guidewire and at least a portion of the dilator in one direction.

The locking mechanism may comprise an attachment connecting to at least one area of the guidewire so that the guidewire cannot be inadvertently advanced too far into the patient, resulting in intravascular guidewire loss or embolization.

The locking mechanism can be configured to maintain a maximum guidewire length beyond the needle tip when advanced. The locking mechanism can be configured to retain the guidewire to the access device so that the guidewire is not misplaced or lost in the patient's body.

In some embodiments, the locking mechanism (which can be adjustable) limits the extent to which the guidewire can be moved (e.g., advanced) relative to the needle. In some modes, a groove or recess can be disposed at a proximal region of the guidewire to inhibit the proximal region from disengaging from the locking mechanism and entering the patient. In other modes, the groove or recess can be positioned at other locations along the guidewire to help regulate the length of guidewire that can be advanced from the needle tip. Preferably, an interaction (e.g., interference, engagement, friction, mechanical coupling, adhesion, etc.) exists between the guidewire and the locking mechanism to inhibit relative movement between these components.

These and other aspects of the present invention will become readily apparent to those skilled in the art from the following detailed description of the preferred embodiments, which refers to the attached figures. The invention is not limited, however, to the particular embodiments that are disclosed.

BRIEF DESCRIPTION OF THE DRAWINGS

These and other features, aspects, and advantages of the access device disclosed herein are described below with reference to the drawings of various embodiments, which are intended to illustrate and not to limit the invention. Additionally, from figure to figure, the same reference numerals have been used to designate the same components of an illustrated embodiment. The following is a brief description of each of the drawings.

FIG. 2A is side view of a needle which can be employed to facilitate insertion of the guidewire of FIG. 1 into a patient.

FIG. 2B is a side cross-sectional view of the needle of FIG. 2A taken along line 2B-2B.

FIG. 3A is a plan view of the dilator of the access device of FIG. 1 and includes a locking mechanism.

FIG. 3B is a side cross-sectional view of the dilator of FIG. 3A taken along the lines 3B-3B.

FIG. 10 is a front perspective view of the locking mechanism of FIG. 8 in an open state to allow a guidewire to pass through the locking mechanism as the dilator and the sheath are being threaded over the guidewire.

FIG. 11 is a rear perspective view of the locking mechanism of FIG. 10 in a locked state where the dilator and the sheath is further threaded over the guidewire until the locking mechanism interlocks with the guidewire stop on the guidewire.

FIG. 11A is an enlarged partial side view of the locking mechanism of FIG. 11 interlocked with the guidewire stop of FIG. 7A on the guidewire.

FIG. 11B is an enlarged partial side view of the locking mechanism of FIG. 11 interlocked with the guidewire stop of FIG. 7B on the guidewire.

FIG. 12A is a side cross-sectional view of the needle of FIG. 2A penetrating a body.

FIG. 12B is an enlarged side cross-sectional view of a distal end of the needle of FIG. 12A which is circled by line 12B-12B.

FIG. 13A is a side cross-sectional view of the needle of FIG. 12A where the needle has penetrated the vasculature.

FIG. 13B is an enlarged side cross-sectional view of a distal end of the needle of FIG. 13A which is circled by line 13B-13B.

FIG. 16A is a side cross-sectional view of the dilator and the sheath of FIG. 1 that have been slid along the exterior portion of the guidewire of FIG. 15 until the locking mechanism in the dilator interlocks with the guidewire stop.

FIG. 16B is an enlarged side cross-sectional view of a portion of the dilator and the sheath of from FIG. 16A which is circled by line 16B-16B.

FIG. 23A is a front view of an embodiment of a locking mechanism.

FIG. 23B is a rear view of the locking mechanism of FIG. 23A.

FIG. 23C is a side cross-sectional view of the locking of FIG. 23A taken along the lines 23C-23C.

FIG. 24A is a side cross-sectional view of the locking mechanism of FIG. 23A with a guidewire inserted through the locking mechanism.

FIG. 24B is a side cross-sectional view of the locking mechanism of FIG. 24A interlocked with the guidewire.

FIG. 25A is a front view of an embodiment of a locking mechanism.

FIG. 25B is a side cross-sectional view of the locking of FIG. 25A taken along the lines 25B-25B.

FIG. 26A is a side cross-sectional view of the locking mechanism of FIG. 25A adhered to a dilator with a guidewire inserted through the locking mechanism.

FIG. 26B is a side cross-sectional view of the locking mechanism of FIG. 25A interlocked with the guidewire.

FIG. 28A is a front view of an embodiment of a locking mechanism.

FIG. 28B is a rear view of the locking mechanism of FIG. 28A.

FIG. 28C is a side cross-sectional view of the locking of FIG. 28A taken along the lines 28C-28C.

FIG. 29A is a side cross-sectional view of the locking mechanism of FIG. 28A located within a dilator and having a guidewire inserted through the locking mechanism.

FIG. 29B is a side cross-sectional view of the locking mechanism of FIG. 29A interlocked with the guidewire.

DETAILED DESCRIPTION

Figure 1:
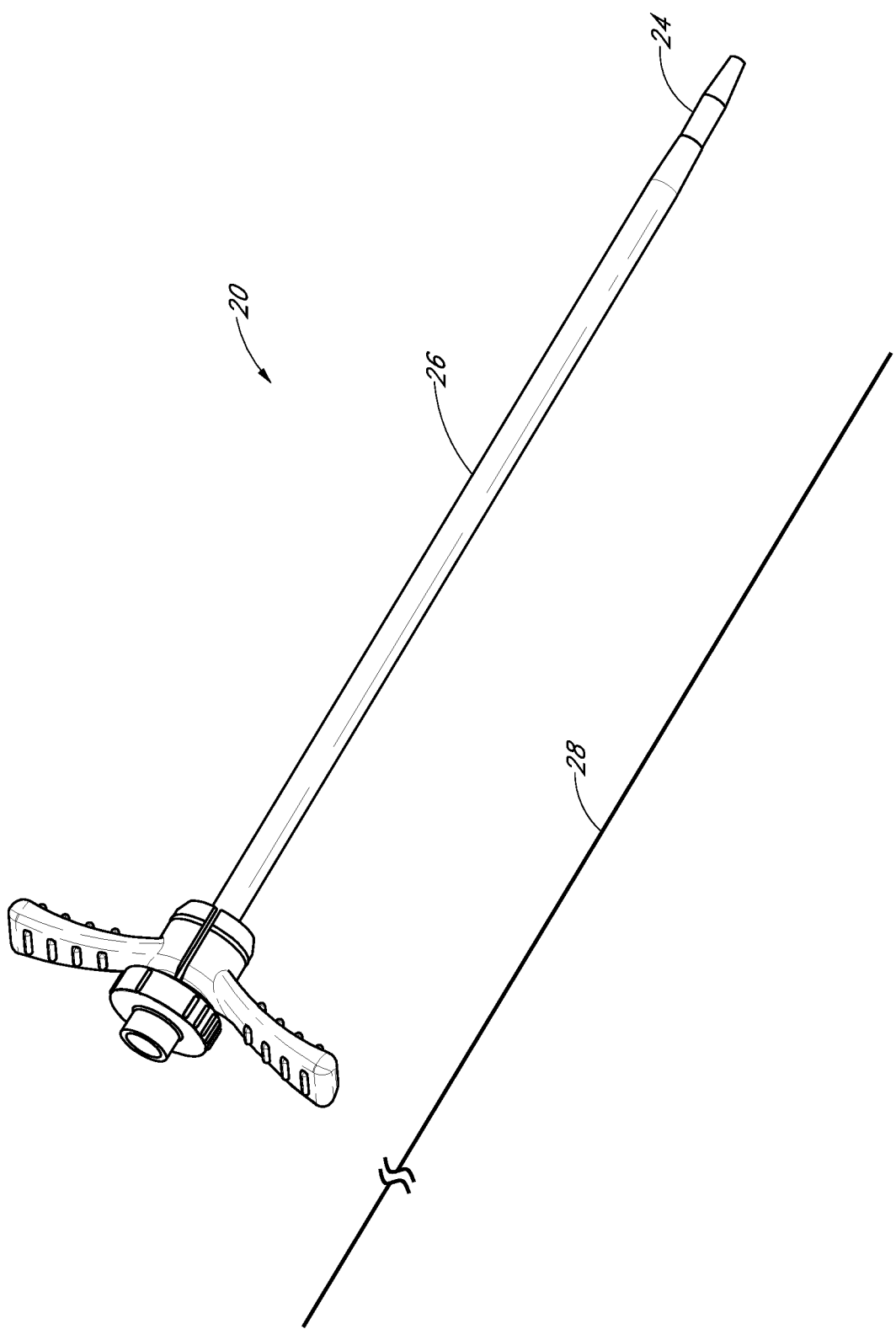
FIG. 1 is a perspective view of an embodiment of an access device including a dilator coaxially aligned with a sheath. A guidewire is also shown.

The present disclosure provides an access device for the delivery of a medical article (e.g., catheter or sheath) to a blood vessel or drainage site. FIG. 1 illustrates an access device 20 that is configured to be inserted into a blood vessel (e.g., a vein or an artery) in accordance with an embodiment discussed herein. While the access device is described below in this context (i.e., for vascular access), the access device also can be used to access and place a medical article (e.g., catheter or sheath) into other locations within a patient's body (e.g., a drainage site) and for other purposes (e.g., for draining an abscess).

The access device, in some embodiments, is disclosed in the context of placing an exemplary single-piece, tubular medical article into a body space within a patient. Once placed, the tubular article can then be used to receive other medical articles (e.g., catheters, guidewires, etc.) to provide access into the body space and/or be used to provide a passage way for introducing fluids into the body space or removing (e.g., draining) fluids from the body space. As shown in the illustrated embodiment, the tubular medical article can be a sheath or catheter that is configured primarily to provide a fluid passage into a vein. However, the current disclosure should not be interpreted as being limited to the placement of single piece sheaths or catheters, or to the subsequent insertion of a medical article via the sheath or catheter. Instead, it will be understood by one of skill in this art, in light of the current disclosure, that the access device disclosed herein also can be successfully utilized in connection with placing one or more other types of medical articles, including other types of sheaths, fluid drainage and delivery tubes, and single or multi-lumen catheters directly in the patient or indirectly via another medical article.

For example, but without limitation, the access device disclosed herein can be configured to directly or indirectly place central venous catheters, peripherally inserted central catheters, hemodialysis catheters, surgical drainage tubes, tear-away sheaths, multi-piece sheaths, scopes, as well as electrical conduit for wires or cables connected to external or implanted electronic devices or sensors. The medical articles listed herein may be directly placed in the patient via the dilator and guidewire of the access device or subsequently placed within the patient via a medical article that was placed within the patient via the dilator and guidewire of the access device.

The embodiments disclosed herein are not limited to co-axial insertion of a single medical article. For example, two catheters may be inserted in the patient via an inserted sheath or a second catheter may be inserted in the patient via an inserted first catheter. In some instances, the medical article inserted via the dilator and guidewire can form a lumen that is in addition to the lumen(s) of the subsequently inserted medical article. One skilled in the art can also find additional applications for the devices and systems disclosed herein. Thus, the illustration and description of the access device in connection with a sheath (e.g., for micro puncture applications) is merely exemplary of one possible application of the access device.

FIG. 1 is a perspective view of an embodiment of an access device 20 that includes a dilator 24 coaxially aligned with a sheath 26. A guidewire 28 is also shown. The components of the access device 20 illustrated in FIG. 1 include a dilator 24 and a sheath 26. In the illustrated embodiment, the access device 20 also includes the guidewire 28. The sheath 26 can be coaxially mounted on the dilator 24. The telescoping nature of the access device's components can also be accomplished by arranging the components with their axes arranged substantially parallel rather than coaxially (e.g., a monorail-type design).

Each of these components includes a luminal fitting at a terminal end or transition (e.g., a hub) and elongated structure that extends from the fitting. Thus, in the illustrated embodiment, the dilator 24 includes a dilator shaft 36 that extends distally from a dilator hub 38, and the sheath 26 includes a sheath body 40 that extends distally from a sheath hub 42. In certain embodiments, the guidewire 28 includes a guidewire hub or cap.

With reference to FIGS. 3B-4C, the access device 20 further includes a stopper or locking mechanism 30. The locking mechanism 30 provides one or more interlocks or interconnections between the locking mechanism 30 and the guidewire and/or one or more other components of the access device 20. In certain embodiments, the locking mechanism 30 provides a first interlock between the locking mechanism 30 and the guidewire 28. In certain embodiments, the locking mechanism 30 further provides a second interlock between the locking mechanism 30 and another component of the access device 20. For example, in certain implementations the first and second interlocks of the locking mechanism 30 can engage with the guidewire 28 and the dilator 24, respectively. The locking mechanism 30 need not include both first and second interlocks. In certain embodiments, the locking mechanism 30 further locks to another component of the access device 20. For example, the locking mechanism 30 can include an interlock for locking to the sheath 26.

The phrase "interlock" means a feature of the locking mechanism 30 which inhibits movement of the locking mechanism 30 in at least one direction relative a component of the access device 20. An interlock can be an interaction (e.g., interference, engagement, friction, mechanical coupling, mechanical interconnection, mechanical interplay, adhesion, etc.). In certain embodiments, for example, such features include one or more structures of the locking mechanism 30 such as tabs, teeth, grooves, etc. as well as a size or shape of the locking mechanism 30 itself. For example, an outer portion of the locking mechanism 30 could be sized and shaped so as to inhibit movement of the locking mechanism 30 relative to an inner surface of a component of the access device 20 via contact between the outer portion and the inner surface.

The locking mechanism 30 is configured to inhibit a proximal portion of the guidewire 28 from being advanced too far through the dilator 24. Advancing the guidewire 28 beyond a proximal end of the dilator 24 risks the possibility of intravascular guidewire loss. Further, even if the guidewire 28 is not advanced beyond the proximal end of the dilator 24, when the dilator 24 is withdrawn from the sheath 26 there is a risk that any friction occurring between flowing blood and a portion of the guidewire 28 inserted into the vasculature will draw the guidewire 28 into the vasculature.

In certain embodiments, the locking mechanism 30 allows the guidewire 28 to be withdrawn from the access device 20 generally simultaneously with the dilator 24.

In certain embodiments, an advanced guidewire 28 is inhibited from being withdrawn back into the dilator 24. For example, the interlock between the locking mechanism 30 and the guidewire 28 can inhibit proximal and/or distal movement of the guidewire 28 relative to the dilator 24. Such an arrangement can reduce the risk of breaking off a distal end of the guidewire 28 and having the distal end of the guidewire 28 enter the vasculature.

FIG. 2A is side view of a needle 22 which can be employed to facilitate insertion of the guidewire 28 from FIG. 1 into a patient. FIG. 2B is a side cross-sectional view of the needle 22 of the embodiment depicted in FIG. 2A taken along line 2B-2B. The needle 22 includes a needle body 32 and a needle hub 34. As best seen in FIG. 2B, the needle hub 34 is disposed on a proximal end of the needle body 32. The needle body 32 terminates at a distal end near a distal portion 48 of the needle 22, and the needle hub 34 lies at a proximal portion 50 of the needle 22.

The needle body 32 preferably has an elongated tubular shape having a circular, constant-diameter interior bore 54 and a circular, constant-diameter exterior surface. In other embodiments, however, the needle body 32 can have other bore and exterior shapes (such as, for example, but without limitation, an oval cross-sectional shape). The interior or exterior of the needle 22 can also include grooves or channels. The grooves or channels may guide fluids within the needle bore either around or to certain structures of the needle 22 or within the needle 22 (e.g., around the guidewire 28). In some embodiments, the grooves or channels may assist in maintaining a desired orientation of the needle 22 with respect to the dilator 24.

The needle body 32 has a sufficiently long length to access a targeted subcutaneous body space and has a sufficient gauge size to withstand the insertion forces when accessing the body space without causing undue trauma. For many applications, the needle body 32 can have a length between 3-20 cm (e.g., between 3-10 cm). For example, to access a body space (e.g., a vessel) in the thorax of an adult human, the needle body 32 preferably has a length of 7 cm or greater, and more preferably has a length of 9 cm or greater, and most preferably has a length of 9 to 10 cm. The size of the needle 22 preferably is 18 gauge or smaller (e.g., between 18-28 gauge or between 18-26 gauge for micro-puncture applications (peripheral IVs)). For applications with a neonate, the length and gauge of the needle body 32 should be significantly shorter and smaller, for example between 3-4 cm and between 26-28 gauge. The needle body 32 can have a bevel tip 52 disposed on the distal portion 48.

As explained below in greater detail, the guidewire 28 is introduced through a hollow portion 68 of the needle hub 34, through the needle body 32, and into a punctured vessel. After removing the needle 22 from the patient, the remaining guidewire 28 allows the healthcare provider to guide the dilator 24 and sheath 26 into the vessel.

FIG. 3A is a plan view of a dilator 24 that can be used with the access device 20 of FIG. 1 and includes a locking mechanism 30. FIG. 3B is a side cross-sectional view taken along the lines 3B-3B in FIG. 3A. The illustrated dilator 24 comprises a dilator shaft 36, a dilator hub 38, a distal region 70, and a proximal region 72.

Figure 4A:
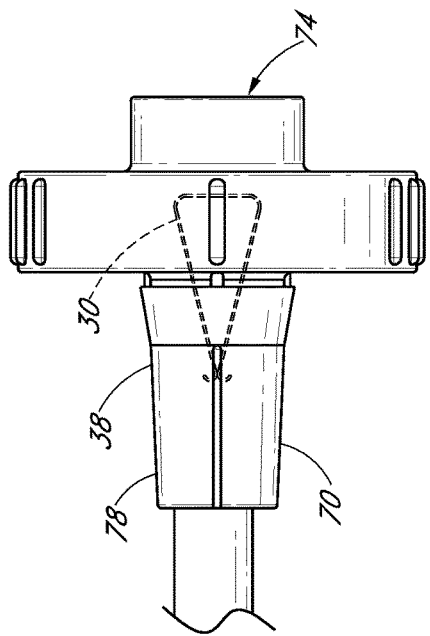
FIG. 4A is an enlarged view of a portion of the dilator of FIG. 3A which is circled by line 4A-4A. The dilator includes a receptacle configured to receive the locking mechanism.

FIG. 4A is an enlarged view of a portion of the dilator 24 illustrated in FIG. 4A which is circled by line 4A-4A. The dilator 24 includes a receptacle 74. In certain embodiments, the receptacle is configured to receive the locking mechanism 30. However, the locking mechanism 30 need not reside within the dilator 24. In certain embodiments, the locking mechanism 30 resides on top of the dilator 24 or outside the dilator 24 as long as the guidewire 28 passes through the locking mechanism 30.

In certain embodiments, the receptacle 74 is sized and shaped so as to allow the locking mechanism 30 to be housed in the dilator hub 38. The locking mechanism 30 may be removed from the receptacle 74 after interlocking with the guidewire 28.

The locking mechanism 30 can be removably engaged with at least a portion of the dilator hub 38 so that the locking mechanism 30 can move in or out of the receptacle 74 when the dilator hub 38 is slid in a proximal or distal direction, respectively, along the guidewire 28. For example, the locking mechanism 30 may be removably held within the receptacle 74 via any suitable interaction (e.g., interference, engagement, friction, mechanical coupling, adhesion, etc.). In certain embodiments, once the locking mechanism 30 interlocks with the guidewire 28 and then abuts a surface of the receptacle 74, further distal movement of the guidewire 28 relative to the dilator 24 is prevented. In such an embodiment, the locking mechanism 30 interlocks with the guidewire 28 so that the guidewire 28 and locking mechanism 30 move in unison during removal of the guidewire 28. In some embodiments, once the locking mechanism 30 interlocks with the guidewire 28, further proximal movement of the guidewire 28 relative to the dilator 24 may be sufficient to overcome the interactive force removably holding the locking mechanism 30 within the receptacle 74. For example, the locking mechanism 30 may be removed from the receptacle 74 after the locking mechanism 30 is engaged to the guidewire 28 by applying a continuing pulling force to move the guidewire 28 in a proximal direction relative to the dilator 24. In certain embodiments, one or more walls such as bottom surface 58 of the receptacle 74 prevent distal movement of the locking mechanism 30 relative to the receptacle 74.

Figure 4B:
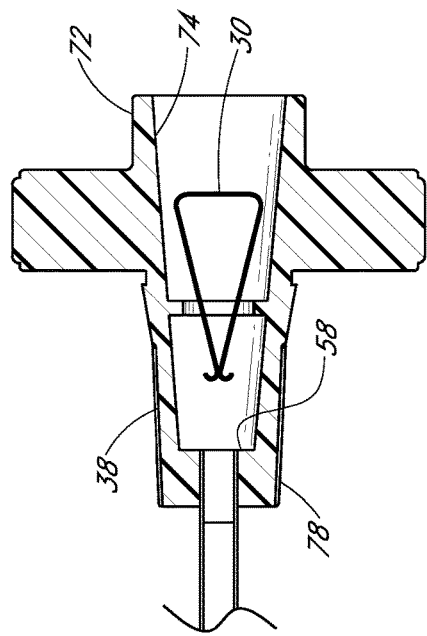
FIG. 4B is a cross-sectional view of the dilator of FIG. 4A taken along line 4B-4B of FIG. 4C.
Figure 4C:
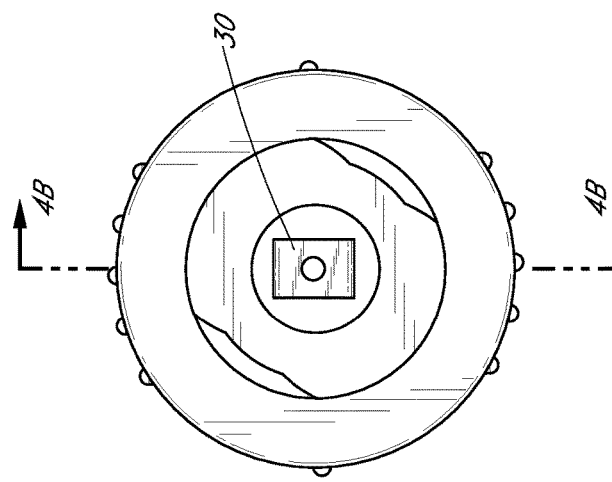
FIG. 4C is an end view of the dilator of FIG. 4A looking in a distal direction.

FIG. 4B is a cross-sectional view of the dilator 24 depicted in FIG. 4A taken along line 4B-4B of FIG. 4C. FIG. 4C is an end view of the dilator 24 depicted in FIG. 4A looking in a distal direction.

The dilator hub 38 may include locking structures at the proximal region 72 and the distal region 70 of the dilator 24. Each locking structure may be a luer type or other type of connection. In the illustrated embodiment, the dilator hub 38 comprises a luer connection 78. In some embodiments, the luer connection 78 (e.g., a male luer slip connector) can be configured to engage to the sheath hub 42 (e.g., a female luer slip connector) on the sheath 26 illustrated in FIG. 5B. Additionally, the male-female lure slip connectors on these components can be reversed.

The color of the dilator 24 may be selected to enhance the contrast between the blood or other fluid and the dilator 24. During blood flash, for example, blood is observed flowing between the dilator 24 and the sheath 26 to confirm proper placement in a blood vessel. To increase the visibility of the fluid as the fluid flows between the sheath 26 and dilator 24, the sheath 26 is preferably manufactured from a clear or transparent material with the dilator 24 having a color that contrasts with the color of the fluid. For example, the dilator 24 may have a white color to enhance its contrast with red blood. Other colors of dilator 24 could be employed depending on the color of the fluid and the degree of contrast desired. Further, only a portion of the dilator 24 in the region of the blood flash can have the contrasting color with the remainder having a different color.

In use, the dilator 24 expands an opening or passage created by the needle 22. The expanded passage facilitates subsequent introduction of the sheath 26. The needle 22 allows the introduction of the guidewire 28, and subsequently the dilator 24 and finally the sheath 26 into a patient's body.

Figure 5A:
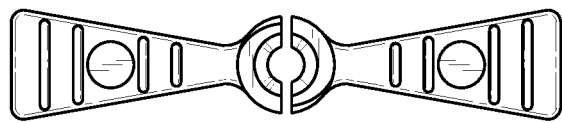
FIG. 5A is a proximal end view of the sheath of the access device of FIG. 1.
Figure 5B:
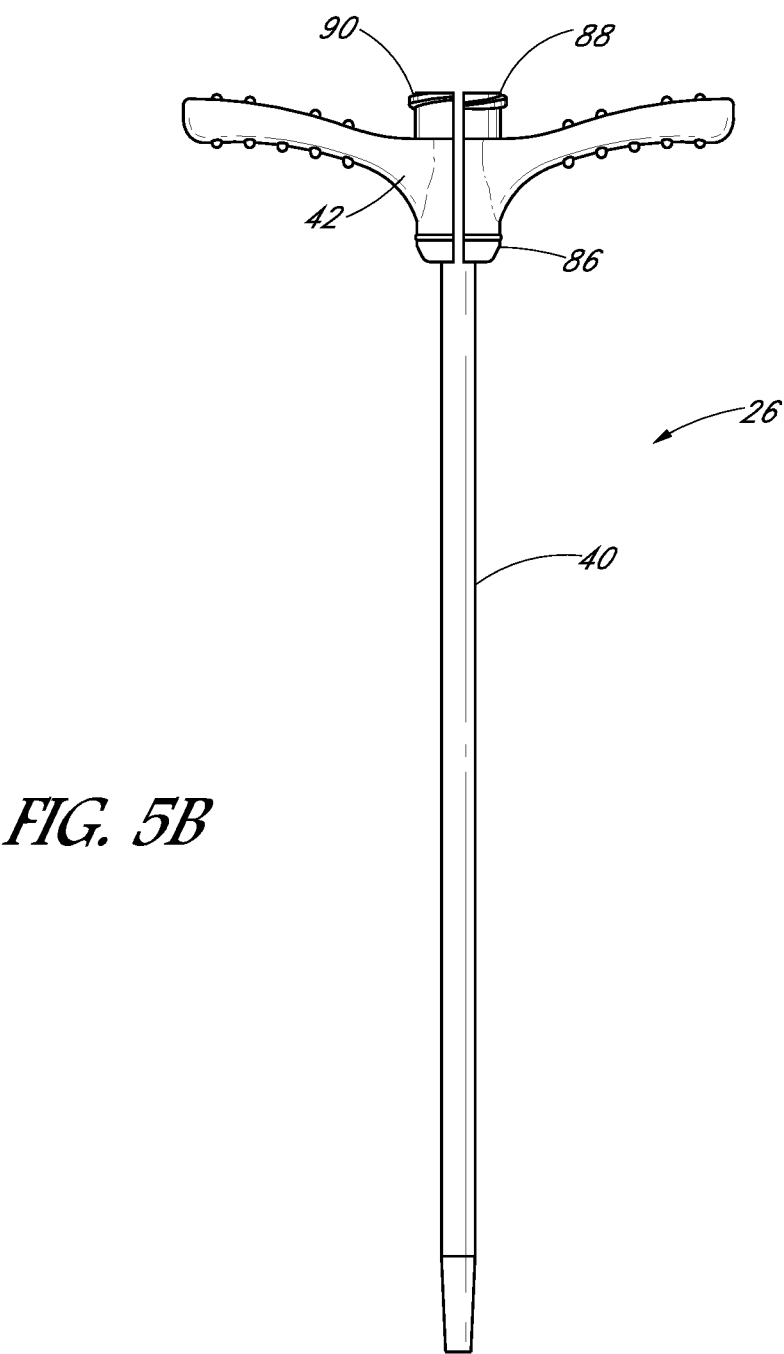
FIG. 5B is a side view of the sheath of FIG. 5A.

FIG. 5A is an end view of a sheath 26 that can be used with the access device 20 of FIG. 1. FIG. 5B is a side view of the sheath 26 depicted in FIG. 5A. The sheath 26 may comprise a sheath body 40, a sheath hub 42, a distal region 86, and a proximal region 88. The sheath body 40 may be made partially or completely from clear, translucent, transparent, or semi-opaque material. The sheath body 40 can also include one or more radiopaque markers, such as, for example, barium sulfate stripes. In a preferred embodiment, the sheath includes two such radiopaque stripes disposed on diametrically opposite sides of the body 40.

The sheath body 40 may be a single piece sheath through which a catheter or other medical article is inserted into the vessel. In such an embodiment, the sheath body 40 forms a conduit for insertion of the catheter or other medical article. In addition to providing a conduit, the sheath 26 or a portion of the sheath can form a lumen that is in addition to the lumen(s) of the catheter. For example, an equivalent to a triple lumen catheter can be formed by inserting a dual lumen catheter through the sheath body 40 with the sheath body 40 itself forming a third lumen.

It may be advantageous to remove a portion or the entire sheath body 40 depending on the type of catheter or medical article that is to be inserted into the vessel after employing the access device 20. For example, after the catheter or other medical article is inserted into the vessel, a portion of the sheath body 40 can be separated or peeled-away and removed. A peel-away sheath can include perforations, serrations, skives, or other structures, or include other materials (e.g., PTFE with bismuth) to allow the physician or healthcare provider to remove easily a portion or the entire sheath body 40.

The sheath hub 42 may include a luer slip connection 90. The luer slip connection 90 may comprise a locking or attaching structure that mates or engages with a corresponding structure. For example, the luer slip connection 90 can be configured to engage with the luer connection 78 of the dilator hub 38.

The sheath hub 42, as best seen in FIG. 5A, preferably is designed so that the luer connection 78 of the dilator hub 38 can enter the sheath hub 42 substantially unobstructed. However, in use, once the sheath hub 42 is placed at a desired location over the dilator shaft 36, the physician or healthcare provider can push, pull, or twist the sheath hub 42 and possibly disengage or engage the luer slip connection 90 with a corresponding connector on another medical article. The luer slip connection 90 creates a mechanical fit so that the dilator hub 38 and the sheath hub 42 are releasably interlocked. The sheath hub 42 preferably engages with the corresponding luer connection 78 on the dilator hub 38. Preferably, the locked position can be disengaged or engaged by pulling, squeezing, pushing or twisting the dilator hub 38 relative to the sheath hub 42.

In additional embodiments, the sheath hub 42 may comprise radially extending wings or handle structures to allow for easy release and removal of the sheath body 40 from other parts of the access device 20. In some applications, the wings are sized to provide the healthcare provider with leverage for breaking apart the sheath hub 42. For example, the sheath hub 42 may comprise a thin membrane connecting the halves of the sheath hub 42. The membrane is sized to keep the halves of the sheath hub 42 together until the healthcare provider decides to remove the sheath hub 42 from the access device. The healthcare provider manipulates the wings to break the membrane and separate the sheath hub 42 into removable halves.

Figure 6:
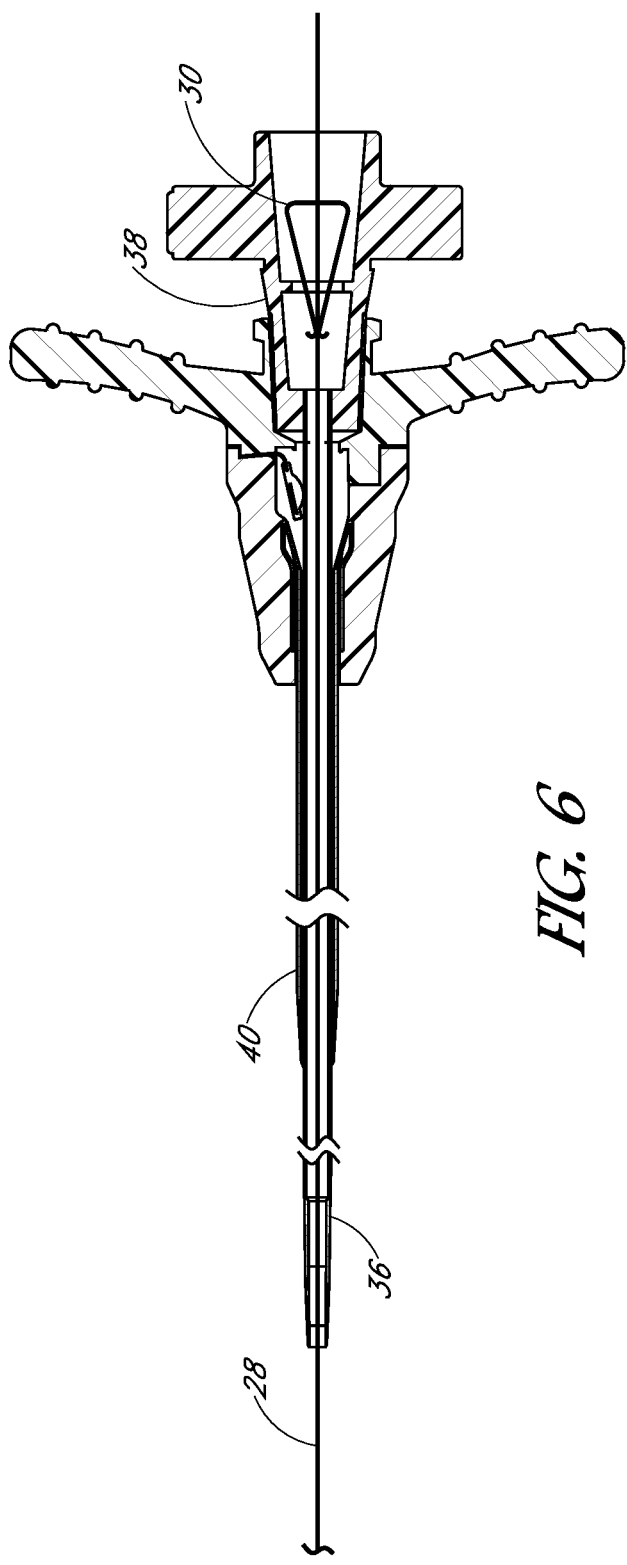
FIG. 6 is a cross-sectional view of the access device of FIG. 1 after the access device has been threaded over the guidewire.

FIG. 6 is a side cross-sectional view of the access device 20 depicted in FIG. 1 after the access device 20 has been threaded over the guidewire 28. Thus, in the illustrated embodiment, the dilator 24 includes the dilator shaft 36 that extends distally from the dilator hub 38, and the sheath 26 includes the sheath body 40 that extends distally from the sheath hub 42. In certain embodiments, the guidewire 28 includes a guidewire hub or cap (not shown). In the illustrated embodiment, the dilator 24 and the sheath 26 are releasably interlocked at a proximal end of the access device 20. In some embodiments, the releasable interlock between the dilator 24 and the sheath 26 is a linear interlock where the sheath 26 is locked to the dilator 24. The relative positioning of the terminal ends of the dilator 24 and the sheath 26 are shown in FIG. 6. For example, the terminal end of the dilator body 36 extends beyond the terminal end of the sheath 26.

Figure 7A:
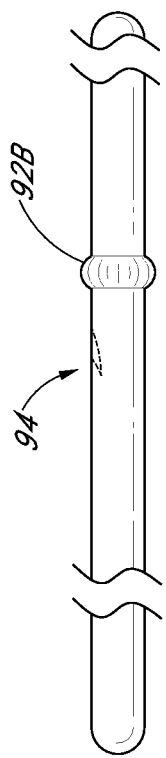
FIG. 7A is a view of a proximal region of an embodiment of the guidewire depicted in FIG. 1 showing a guidewire stop configured to be used by a locking mechanism to secure to the guidewire.
Figure 7B:
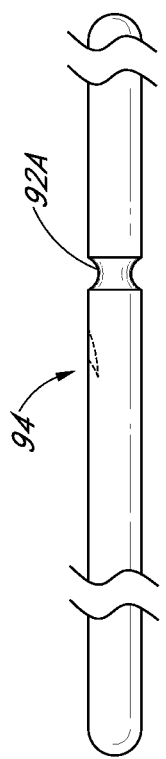
FIG. 7B is a view of a proximal region of another embodiment of the guidewire depicted in FIG. 1 showing a guidewire stop configured to be used by a locking mechanism to secure to the guidewire.

FIGS. 7A and 7B are various views of a proximal region 94 of the guidewire 28 depicted in FIG. 1 showing a guidewire stop 92A, 92B configured to be used by the locking mechanism 30 to secure to the guidewire 28. In certain embodiments, the guidewire stop 92A, 92B is one or more features of the guidewire 28 which allow the locking mechanism 30 to engage the guidewire 28. In the embodiment illustrated in FIG. 7A, the guidewire stop 92A is in the form of an annular groove defined by one or more ridges (e.g., two ridges). The groove may be sized and configured to engage with the corresponding locking mechanism 30, as described herein. While the guidewire stop 92A is illustrated as a groove, it will be understood by one having skill in the art that the guidewire stop may comprise any shape or size suitable to engage the locking mechanism 30. For example, as illustrated in FIG. 7B, the guidewire stop 92B may comprise an outward protrusion configured to inhibit further distal movement of the guidewire 28 relative to the locking mechanism 30 once the guidewire stop 92B abuts and/or engages the locking mechanism 30. The guidewire stop 92B may function in a similar manner as the guidewire stop 92A. In some instances, the guidewire stop 92B may comprise one or more outward protrusions (e.g. cams) protruding from on one or more sides of the guidewire 28. The one or more cams may be sized and configured to separate the opposing clips 80 (as described herein and shown in FIGS. 8 and 9) of the locking mechanism 30 as the one or more cams pass through the opposing clips 80 in a proximal direction relative to the locking mechanism 30. After the one or more cams pass through the opposing clips 80, the opposing clips 80 may close behind the one or more cams to prevent distal movement of the one or more cams relative to the opposing clips 80. Additionally, while the guidewire stop 92A, 92B is illustrated as residing on the proximal region 94 of the guidewire 28, it will be understood by one having skill in the art that the guidewire stop 92A, 92B may be placed at any location along the guidewire 28. In certain other embodiments, the guidewire stop is in the form of a notch, taper, barb, adhesive, magnet, or other feature.

In some instances, the guidewire stop 92A, 92B can be formed by varying the width of the guidewire 28. For example, the guidewire 92B may comprise a portion of the guidewire 28 that comprises an increased width relative to the remainder of the guidewire 28. The increased width portion of the guidewire stop 92B may be followed by a guidewire 28 section of reduced width that is located both proximal and distal to the guidewire stop 92B. The increased width of the guidewire stop 92B may be sized and configured to permit the locking mechanism 30 to engage the guidewire stop 92B, while also being of a sufficient width to inhibit the guidewire stop 92B from passing through the opening 82 of the locking mechanism 30, described herein. The increased width of the guidewire stop 92B can be configured to engage the locking mechanism 30, while also permitting the guidewire stop 92B to pass through the interior bore 54 of the needle 22. For example, an outer width of the guidewire stop 92B may be smaller than an interior diameter of the interior bore 54 of the needle 22. The increased width of the guidewire stop 92B may be formed by any suitable means. For example, the guidewire stop 92B may comprise an annular flange located along the guidewire 28. By way of another example, the guidewire stop 92B may be formed by stamping and/or compressing a portion of the guidewire 28 to form a guidewire stop 92 that comprises a pinched surface with an outwardly protruding increased width along the guidewire 28.

The guidewire stop 92A, 92B is preferably disposed in the proximal region 94 of the guidewire 28 and is configured to engage with the locking mechanism 30 at least when the dilator 24 is threaded over the guidewire 28. Until the guidewire stop 92A, 92B interlocks with the locking mechanism 30 and causes the locking mechanism 30 and/or the guidewire stop 92A, 92B to abut against the wall 58, the healthcare provider can freely manipulate the guidewire 28 within the dilator 24. However, after the guidewire stop 92A, 92B interlocks and then contacts the wall 58, the healthcare provider is prevented from extending the guidewire 28 further in a distal direction relative to the dilator 24.

In certain embodiments, as the guidewire 28 is initially threaded through the dilator hub 38, the locking mechanism 30 closes about the outer surface of the guidewire 28 so as to pinch the guidewire 28. The pinching force, in some instances, may not be sufficient to engage with the guidewire 28. In certain embodiments, the bite force of the locking mechanism 30 on the guidewire 28 is insufficient to prevent movement of the guidewire 28 relative to the locking mechanism 30. The bite force of the locking mechanism 30 on the guidewire 28 may still permit movement of the guidewire 28 relative to the locking mechanism 30 until the locking mechanism 30 interlocks or engages with the guidewire stop 92A, 92B. For example, the locking mechanism 30 may not sufficiently resist passage of the guidewire 28 through the locking mechanism 30 before the locking mechanism 30 engages the guidewire stop 92A, 92B. Once the locking mechanism 30 engages with the guidewire stop 92A, 92B, the locking mechanism 30 inhibits at least further distal movement of the guidewire 28 relative to the locking mechanism 30.

Figure 9:
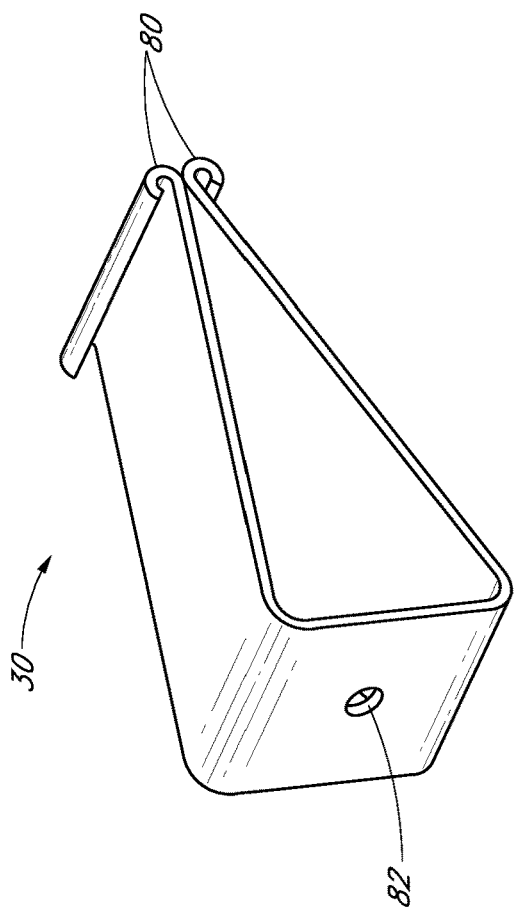
FIG. 9 is a rear perspective view of the locking mechanism from FIG. 8.
Figure 8:
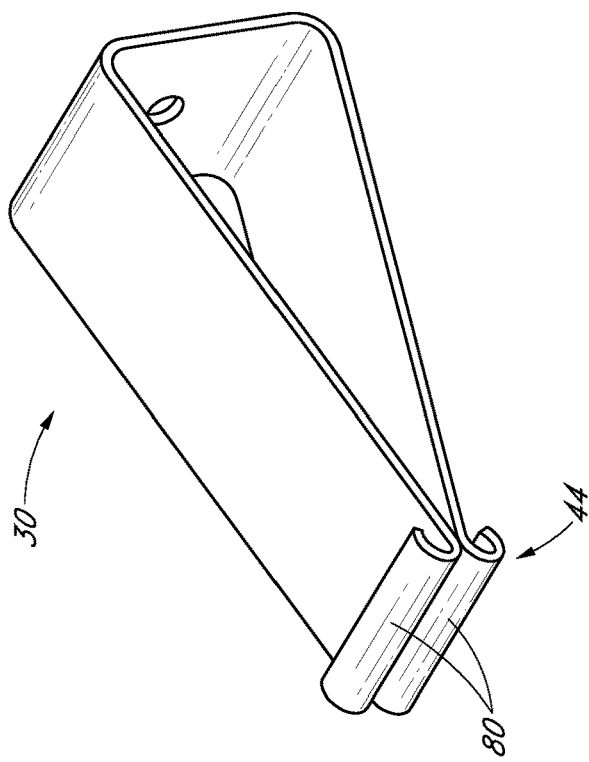
FIG. 8 is a front perspective view of the locking mechanism of FIG. 4A removed from the dilator.

FIG. 8 is a perspective view of the locking mechanism 30 from FIG. 4A removed from the dilator 36. FIG. 9 is an opposite end perspective view of the locking mechanism 30 from FIG. 8. As discussed herein, the dilator hub 38 comprises the locking mechanism 30. In certain embodiments, the locking mechanism 30 is disposed in the sheath 26 or other medical article. The locking mechanism 30 may be configured to lock or secure to the guidewire 28. As shown in FIGS. 8 and 9, the locking mechanism 30 comprises a guidewire lock 44 and an opening 82. The guidewire lock 44 can comprise one or more engaging mechanisms such as a pair of opposing clips, teeth, tabs, or opening, although other types of locking mechanisms comprising tabs and/or slots can also be used.

In the illustrated embodiment, the guidewire lock 44 is configured as a pair of opposing clips 80. The locking mechanism 30 is generally V-shaped and is configured to be biased towards a closed condition, while still permitting the locking mechanism 30 to slide over the guidewire 28 when the guidewire 28 is advanced through the V-shaped locking mechanism 30 and then to spring towards the guidewire 28 and into the guidewire stop 92A, 92B.

FIG. 10 is a view similar to FIG. 8 except the guidewire lock 44 is open or in an unlocked state, allowing the guidewire 28 to pass through the locking mechanism 30 as the dilator 24 and the sheath 26 are threaded over the guidewire 28. The guidewire lock 44 can be biased towards a closed configuration as illustrated in FIG. 8. The degree of bias of the guidewire lock 44 towards the closed condition is selected so that the guidewire 28 can slide through the guidewire lock 44 when the guidewire lock 44 is not in contact or engaged with the guidewire stop 92A, 92B. The guidewire lock 44 is in a locked state when the guidewire lock 44 is engaged with the guidewire stop 92A, 92B (as illustrated in FIGS. 11, 11A, and 11B).

FIG. 11 is a view similar to FIG. 10 but taken from the opposite end of the locking mechanism 30 and with the dilator 24 and the sheath 26 further threaded over the guidewire 28 until the locking mechanism 30 interlocks with the guidewire stop 92A, 92B on the guidewire 28. FIG. 11A is an enlarged partial cross-section view from FIG. 11 of the locking mechanism 30 interlocked with the guidewire stop 92A on the guidewire 28. By way of another example, FIG. 11B is an enlarged partial cross-section view from FIG. 11 of the locking mechanism 30 interlocked with the guidewire stop 92B on the guidewire 28. In the illustrated embodiments, the locking mechanism 30 has slid in the distal direction relative to the guidewire 28 until the locking mechanism 30 interlocks with the guidewire stop 92A, 92B on the guidewire 28. The clips 80 of the guidewire lock 44 can engage a lipped and/or compressed surface such as the guidewire stop 92A, 92B shown in FIG. 7. Once engaged, the guidewire lock 44 inhibits the guidewire stop 92A, 92B from undesired slipping or releasing relative to the locking mechanism 30. The guidewire 28 can essentially carry the locking mechanism 30 and move in unison with the locking mechanism 30. In certain embodiments, the guidewire lock 44 is hinged to provide a bias towards the center of the dilator hub 38. The bias may prevent the secured part of the guidewire 28 from slipping or disengaging from the guidewire lock 44.

The interlocking structure illustrated in FIGS. 8-11 is but one example of the types of cooperating structure that can be included to interconnect or interlock the locking mechanism 30 with the guidewire 28 and/or the dilator 24. The interlocking structure, in some embodiments, does not engage with the guidewire 28 until the dilator 24 is sufficiently threaded over the guidewire 28 to allow the interlocking structure to contact the guidewire lock 44. In this way, the interlocking structure does not inhibit use or appreciably increase contact friction when the healthcare provider is manipulating the guidewire 28 until after the guidewire lock 44 contacts the guidewire stop 92A, 92B.

Figure 27A:
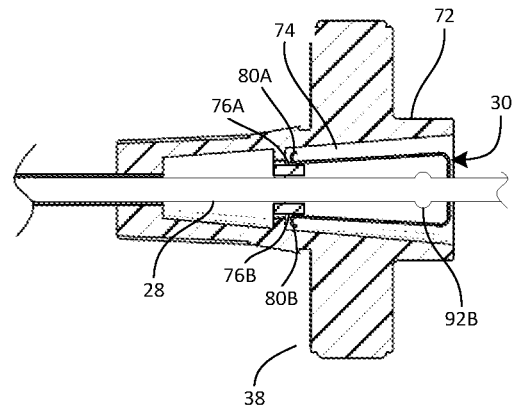
FIG. 27A is a side cross-sectional view of an embodiment of a locking mechanism engaged with a dilator and having a guidewire inserted through the locking mechanism.
Figure 27B:
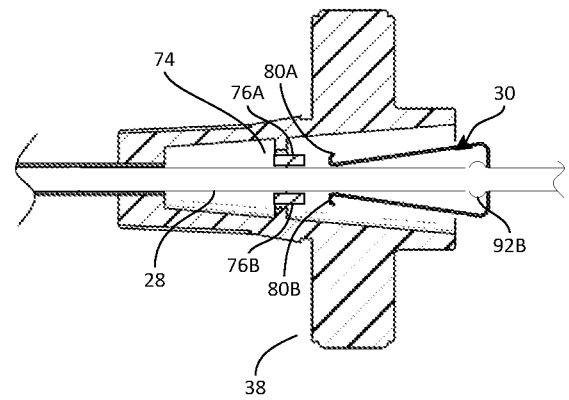
FIG. 27B is a side cross-sectional view of the locking mechanism of FIG. 27A interlocked with the guidewire.

FIGS. 27A and 27B are various views of the locking mechanism 30 and dilator hub 38, according to some embodiments. At least a portion of the locking mechanism 30 (e.g., the opposing clips 80A, 80B shown in FIG. 27A), in some instances, may be engaged with a portion of the dilator hub 38 to initially maintain the locking mechanism 30 in the open state. As shown in FIGS. 27A and 27B, respectively, the locking mechanism 30 may have a first open state positioned on the dilator hub 38 and a second closed state positioned on and/or engaged with the guidewire 28.

As illustrated in FIG. 27A, when the locking mechanism 30 is in the open state, the locking mechanism 30 may be placed along a portion of the dilator hub 38. The locking mechanism 30 can be clamped, preformed, or otherwise positioned over or around at least a portion of the dilator hub 38 to temporarily maintain the locking mechanism 30 in the open state and inhibit the locking mechanism 30 from entering the closed state. An interior surface of the dilator hub 38 may comprise a ledge, groove, ride, or any suitable protrusion configured to engage one or more of the opposing clips 80A, 80B to hold the locking mechanism 30 in the open state before interaction with the guidewire stop.

The protrusion can be sized and configured to extend along any portion and/or length of the receptacle 74 of the dilator hub 38. For example, the protrusion can be configured to be positioned within the receptacle 74 on a distal end or proximal end of the dilator hub 38. For example, the dilator hub 38 may include one or more ledges 76A, 76B configured to engage a corresponding clip 80A, 80B. The protrusion can be configured such that a first portion of the locking mechanism 30 (e.g., a first clip 80A) is positioned along a corresponding portion of the protrusion (e.g., a first ledge 76A), and a second portion of the locking mechanism 30 (e.g., a second clip 80B) is positioned along a corresponding second portion of the protrusion (e.g., a second ledge 76B) to maintain the locking mechanism 30 in the open state. The locking mechanism 230 can be configured to interlock, engage or adhere to the protrusion when initially positioned within the receptacle 74. In some embodiments, the first portion and the second portion of the locking mechanism 30 (e.g., clips 80A, 80B) can adhere at least to the protrusion comprising an adhesive. In some embodiments, the adhesive can extend along an entire inner perimeter of the protrusion. The protrusion can be made of a single unitary body (e.g., an annular ridge) within the dilator hub 38 to that is configured to allow the opposing clips 80A. 80B to position themselves over and/or around the one or more ledges 76A, 76B to temporarily maintain the locking mechanism 30 in the open state.

The locking mechanism 30 can comprise an opening 82 (as shown in FIGS. 8-11) that is sized and configured to selectively permit at least a portion of the guidewire 28 to pass through. The opening 82 can be chamfered to facilitate insertion of the guidewire proximal end through opening 82. An inner diameter of the opening 82, as described herein, can be sufficiently large to permit a portion of the guidewire 28 to reside within and/or pass through the opening 82. However, in some embodiments, the inner diameter of the opening 82 is not large enough to permit at least another portion of the guidewire 28 to pass through the opening 282 (e.g., the guidewire stop 92B). As such, the guidewire stop 92B may generally be too large to fit through the opening 82 and further proximal movement of the guidewire 28 relative to the dilator hub 38 will cause the locking mechanism 30 to transition into the closed state. For example, the guidewire stop 92B can abut against the locking mechanism 30 and cause the locking mechanism 30 to move in a proximal direction relative to the dilator hub 38 and, consequently, detach the one or more clips 80A, 80B from the protrusion (e.g., one or more ledges 76A, 76B) of the dilator hub 38, as described with reference to FIG. 27B.

In some instances, when the locking mechanism 30 transitions from the open state to the closed state, the locking mechanism 30 can be positioned around a portion of the guidewire 28 such that the locking mechanism 30 prevents the guidewire 28 from moving distally beyond the dilator hub 38. As the guidewire 28 is moved in a proximal direction relative to the dilator hub 38 (shown in FIG. 27A), the guidewire stop 92B can abut against and/or engage the locking mechanism 30. Further distal movement of the guidewire stop 92B relative to the dilator hub 38 can cause the guidewire stop 92B to detach the locking mechanism 30 from the protrusion of the dilator hub 38. Removal of the locking mechanism 30 from the protrusion may cause the locking mechanism 30 to transition to the closed state and engage at least a portion of the guidewire 28 (shown in FIG. 27B). In some instances, the first clip 80A and/or the second clip 80B of the locking mechanism 30, once removed from the protrusion of the dilator hub 38, may engage the guidewire 28 to enclose at least a portion of the guidewire 28. The locking mechanism 30 can enclose the guidewire 28 to inhibit access of the engaged portion of the guidewire 28 in a distal direction beyond the dilator hub 38, as described herein. The locking mechanism 30, as described herein, can be biased towards the close state so that when in the locking mechanism 30 is disengaged with the protrusion, the locking mechanism 30 automatically transitions towards the closed state (as illustrated in FIG. 27B).

Other types of locking mechanisms can also be used for this purpose. For example, but without limitation, an annular bead can be located within the dilator hub 38 and biased towards a closed configuration. Once the guidewire stop 92A, 92B contacts the guidewire lock 44, the bead snaps closed about guidewire 28. In some instances, the dilator hub 38 can include one or more annular grooves defined within the receptacle 74. When the bead reaches the annular groove the bead and guidewire 28 are prevented from further distal movement.

In some embodiments, the locking mechanism 30 may comprise one or more finger or tang or cam elements defining the guidewire lock 44 or opening configured to permit the guidewire 28 to pass through the locking mechanism 30. The one or more finger elements can project from a distal end of the locking mechanism 30 toward a proximal end of the locking mechanism 30. The one or more finger elements may permit the guidewire stop 92A, 92B to pass through the guidewire lock 44 or the opening in a proximal direction but inhibit to passage of the guidewire stop 92A, 92B through the guidewire lock 44 or the opening in a distal direction. The guidewire stop 92A, 92B can slide through the opening in a proximal direction through the finger elements. As the guidewire stop 92A, 92B passes through, the finger elements can lock into a biased closed position between the guidewire lock 44 or the opening and the guidewire stop 92A, 92B. This inhibits and/or substantially irreversibly prevents axial movement of the guidewire stop 92A, 92B at least in the distal direction once the guidewire stop 92A, 92B passes through the opening.

As with the illustrated embodiment, the degree of bias of the locking mechanism 30 towards the closed condition is selected so that the guidewire 28 can slide through the locking mechanism 30 when the locking mechanism 30 is not in contact with the guidewire stop 92. Once the locking mechanism 30 contacts and locks to the guidewire stop 92, the healthcare provider can generally simultaneously withdraw the dilator 24 and the guidewire 28 from the sheath 26 without risking the embolization of the guidewire 28. The engagement of the locking mechanism 30 with the guidewire 28 and/or the dilator 24 can occur through simple axial movement of the guidewire 28 relative to the dilator hub 38, as understood from the embodiments described above.

FIG. 12A is a cross-sectional view of the needle 22 illustrated in FIG. 2A penetrating a body 118. FIG. 12B is an enlarged partial cross-sectional view from FIG. 12A of a distal end of the needle 22. In FIG. 13A, the needle 22 has penetrated the vasculature. FIG. 13B is an enlarged partial cross-sectional view from FIG. 13A of a distal end of the needle 22. In use, the bevel tip 52 enters the blood vessel 122.

Figure 14:
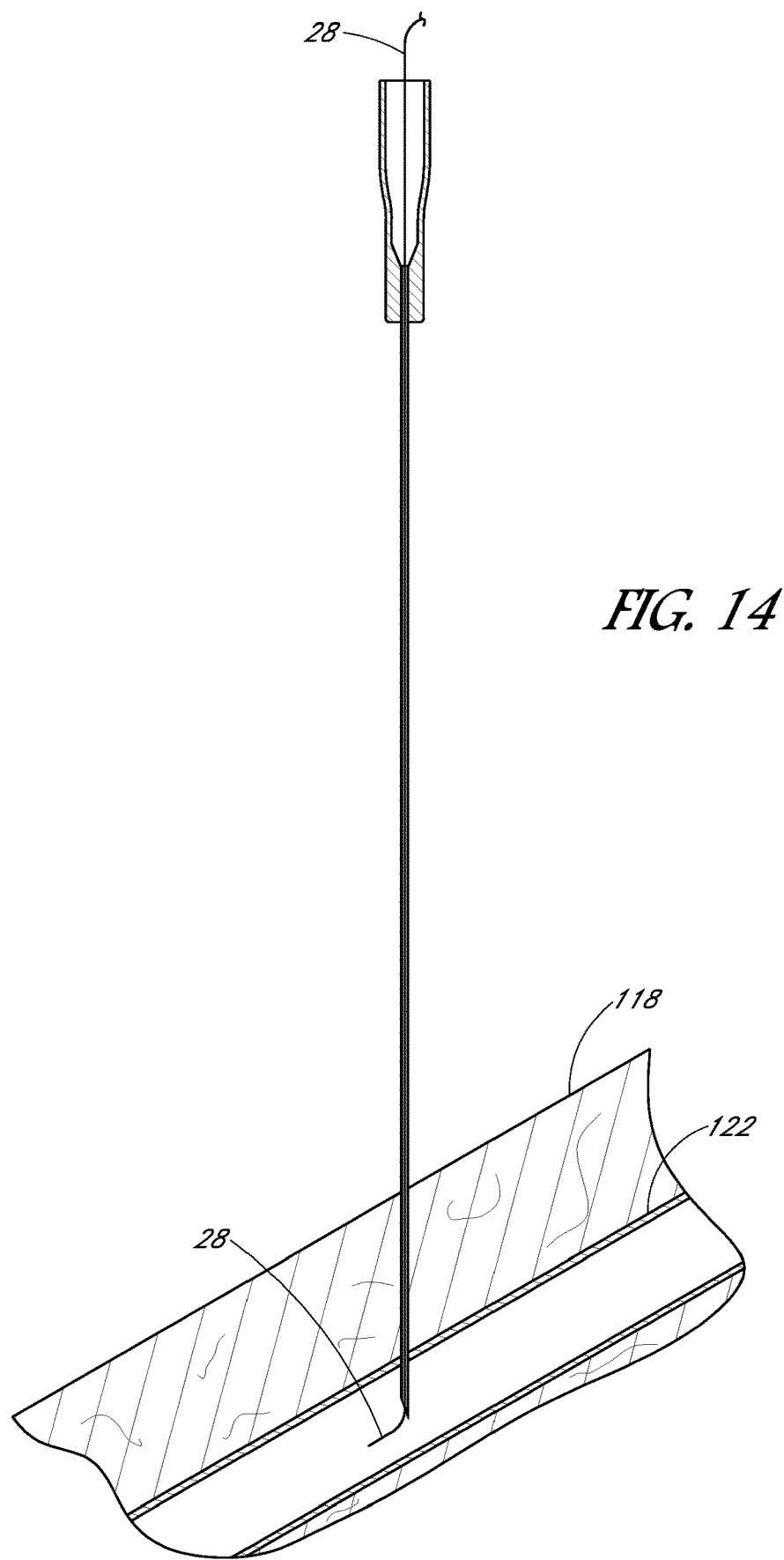
FIG. 14 is a side cross-sectional view of the needle of FIG. 13A where a guidewire has been fed through the needle and into the vasculature of the patient.

FIG. 14 is a cross-sectional view similar to FIG. 13A where a guide wire 28 has been fed through the needle 22 and into the blood vessel 122 of the patient. Once the physician or healthcare provider has located the needle 22 within the target blood vessel 122, the physician or healthcare provider feeds the guidewire 28 into the vasculature. The needle 22 is held still while the guidewire 28 is fed through the needle 22 and into the patient. During the insertion procedure, the guidewire 28 passes through the interior bore 54 of the needle 22.

Figure 15:
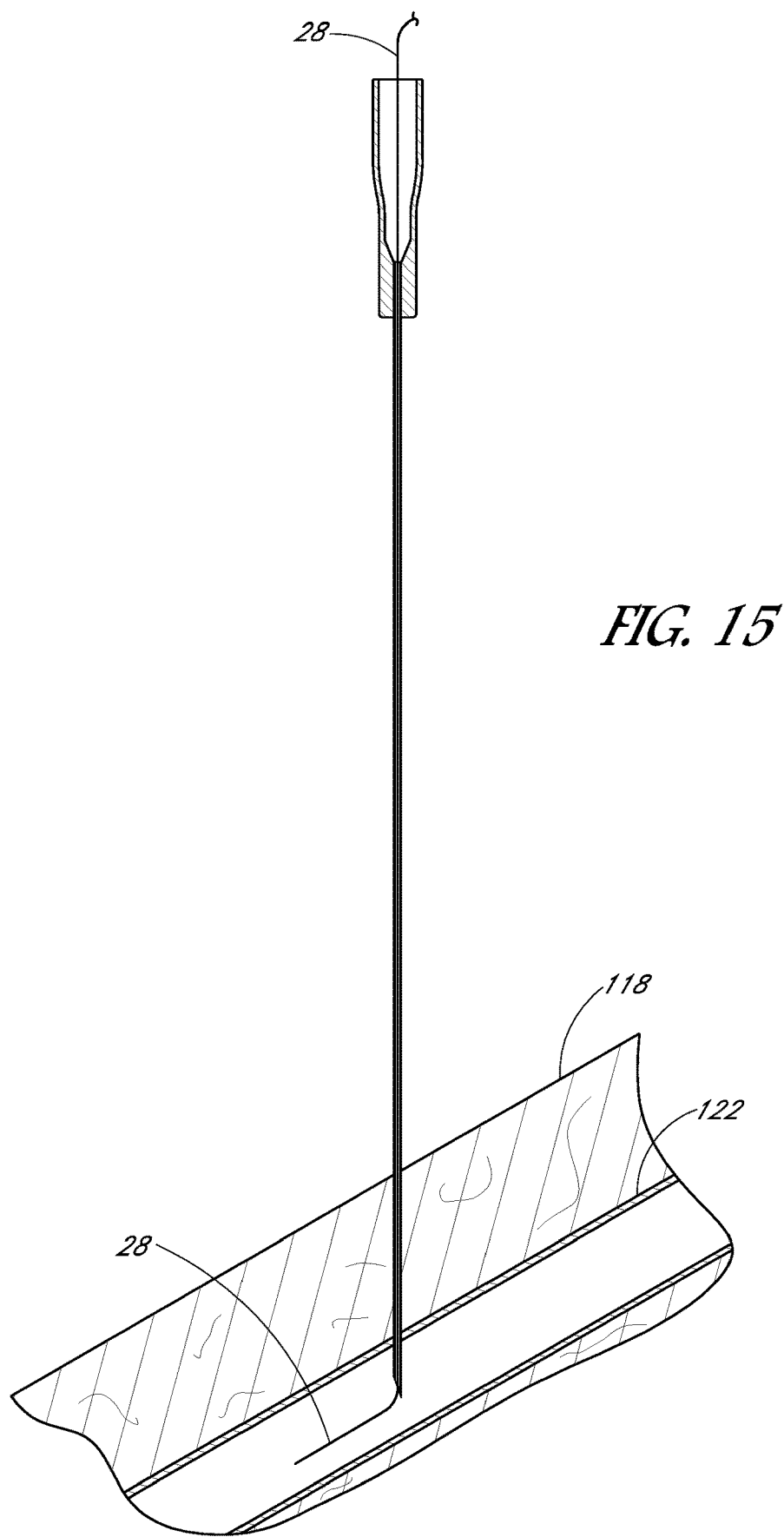
FIG. 15 is a side cross-sectional view of the needle of FIG. 14 where the guidewire has been extended into the vasculature of the patient.

A guide wire advancer as known in the art may be employed when feeding the guidewire 28 through the needle 22. For example, if the guidewire 28 has a curved or J tip, an advancer may be employed to straighten the tip facilitating feeding of the guidewire 28 into the interior bore 54 of the needle 22. FIG. 15 is a cross-sectional view similar to FIG. 14 except the guidewire 28 has been extended further into the vasculature of the patient.

FIG. 16A is a cross-sectional view similar to FIG. 15 where the needle 22 has been removed and the dilator 24 and the sheath 26 have been slid along the exterior portion of the guidewire 28 until the locking mechanism 30 in the dilator 24 interlocks with the guidewire stop 92A, 92B. FIG. 16B is an enlarged partial cross-sectional view from FIG. 16A. The locking mechanism 30 within the receptacle 74 of the dilator 24 has effectively slid in the distal direction relative to the guidewire 28 until the locking mechanism 30 interlocks with the guidewire stop 92 on the guidewire 28. The clips 80 of the guidewire lock 44 can engage a lipped surface such as the guidewire stop 92A, 92B shown in FIGS. 7A and 7B. Once engaged, the guidewire lock 44 prevents the locked part of the guidewire 28 from undesired slipping or releasing relative to the locking mechanism 30. The guidewire 28 can essentially carry the locking mechanism 30 and move in unison with the locking mechanism 30. In certain embodiments, the guidewire lock 44 is hinged to provide a bias towards the center of the dilator hub 38. The bias can prevent the secured part of the guidewire 28 from slipping or disengaging from the guidewire lock 44.

Figure 16C:
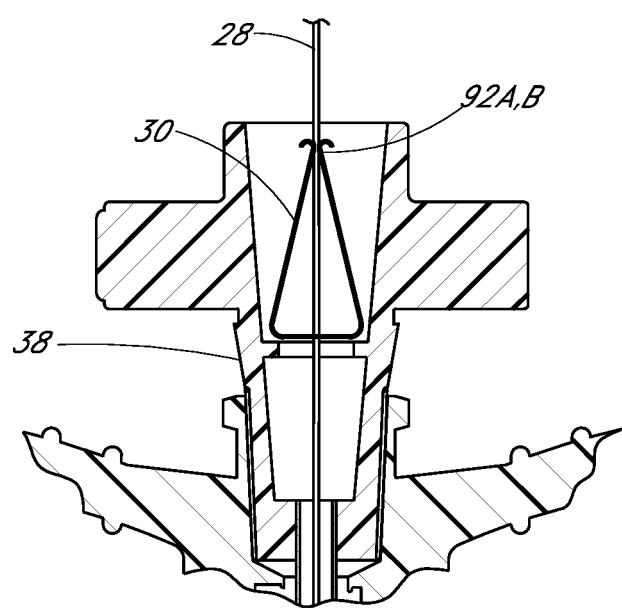
FIG. 16C is an enlarged side cross-sectional view of a portion of the dilator and the sheath similar to FIG. 16B, where the orientation of the locking mechanism is reversed.

In some embodiments, the orientation of the locking mechanism 30 within the dilator hub 38 may be reversed. For example, FIG. 16C is an enlarged partial cross-sectional view similar to FIG. 16B, except where the opposing clips 80 of the locking mechanism 30 (as described herein) are located in a proximal direction from the opening 82 of the locking mechanism 30. While in a reversed orientation (shown in FIG. 16C), the locking mechanism 30 may function in the same manner as described herein; however, the guidewire 28 and the guidewire stop 92A, 92B may pass through the opening 82 prior to passing through or engaging the opposing clips 80, respectively. In such an embodiment, the guidewire stop 92A, 92B and the opening 82 may be sized and configured to permit the guidewire stop 92A, 92B to pass through the opening 82. To further facilitate insertion of the guidewire proximal end through the opening 82, the distal side of opening 82 can be chamfered.

Figure 17:
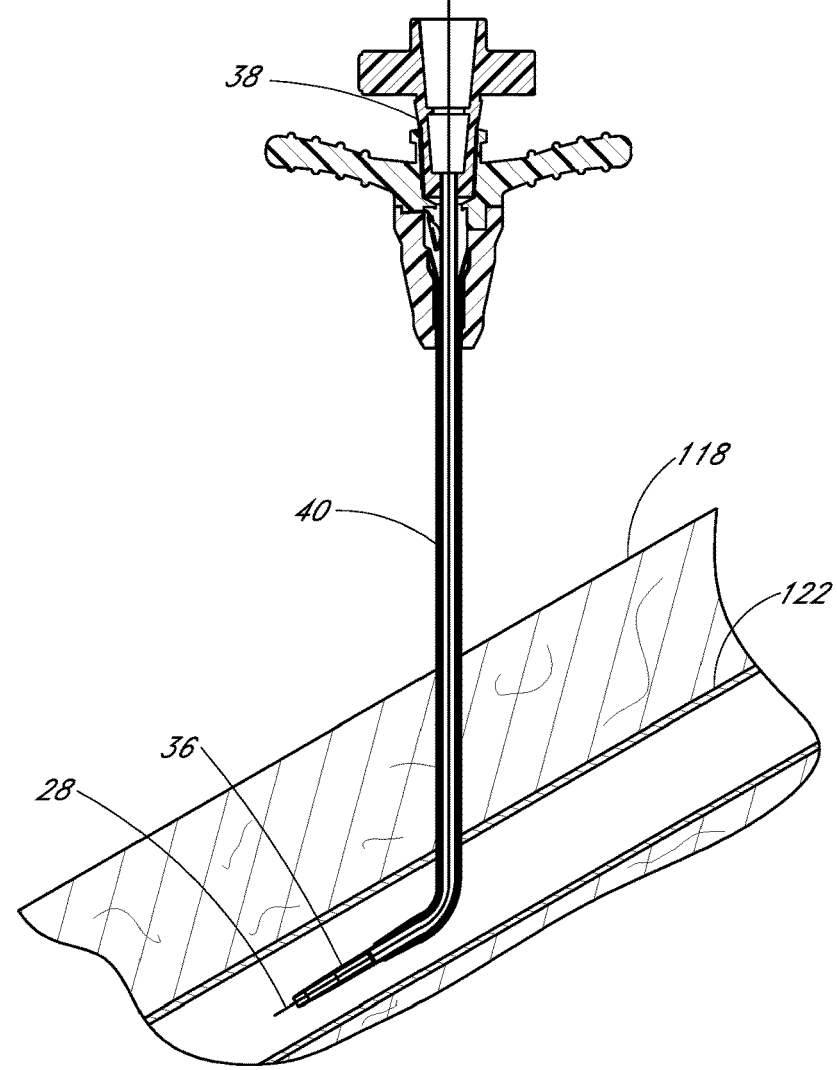
FIG. 17 is a side cross-sectional view of the dilator and the sheath of FIG. 16A where the dilator and sheath have been slid further along the exterior portion of the guidewire and into the patient's vasculature causing the dilator to be spaced from the locking mechanism.

FIG. 17 is a cross-sectional view similar to FIG. 16A where the dilator 24 and sheath 26 have been slid further along the exterior portion of the guidewire 28 and into the patient's vasculature causing the dilator 24 to be spaced from the locking mechanism 30. During threading of the sheath 26 and the dilator 24 over the guidewire 28 and into the blood vessel 122, the guidewire 28 freely slides through the locking mechanism 30 until the guidewire lock 44 interlocks with the guidewire stop 92A, 92B. Once interlocked, the guidewire 28 and the locking mechanism 30 can move in unison. In this configuration, the guidewire 28 is prevented from exiting a distal end of the dilator 24 in a distal direction and being lost in the patient.

Figure 18:
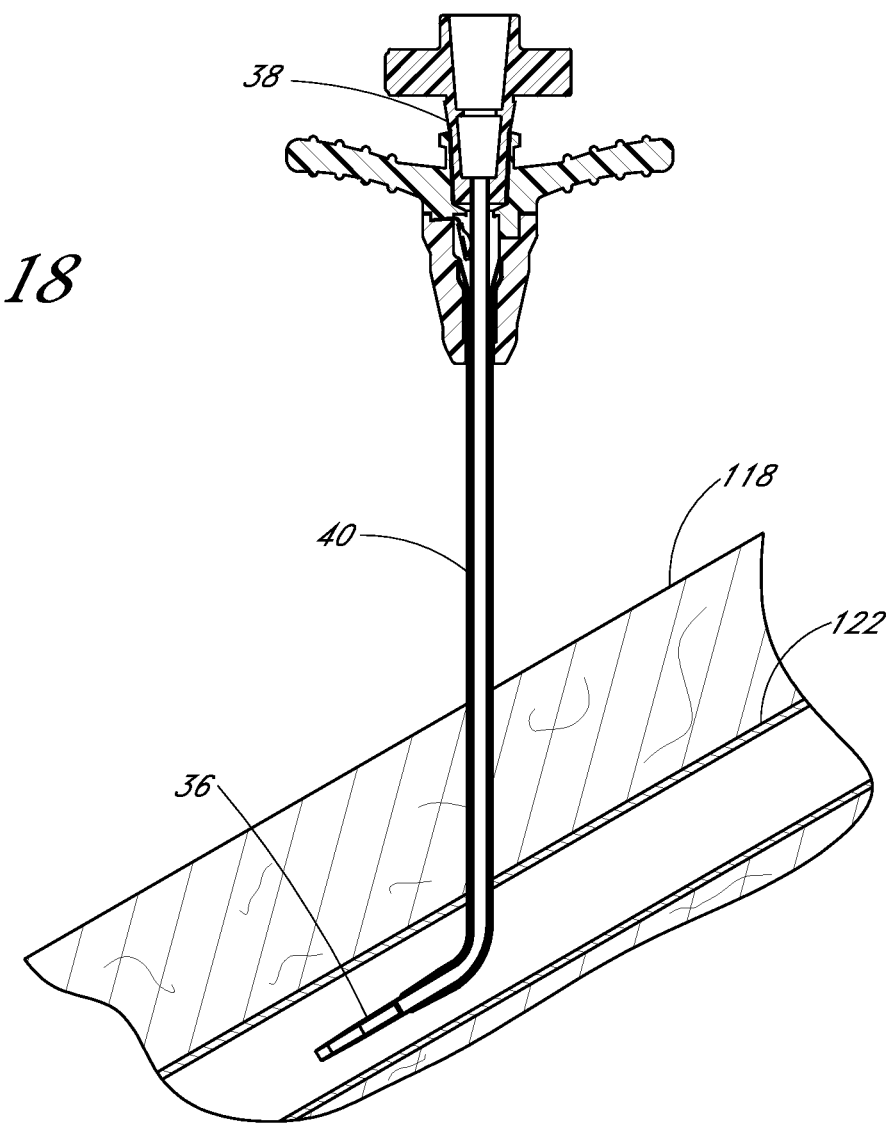
FIG. 18 is a side cross-sectional view of the dilator and the sheath of FIG. 17 where the guidewire and interlocked locking mechanism have been withdrawn from the dilator and the sheath.

FIG. 18 is a cross-sectional view similar to FIG. 17 where the guidewire 28 and interlocked locking mechanism 30 have been withdrawn from the dilator 24 and the sheath 26. In certain embodiments, the healthcare provider can instead withdraw the dilator 24 until the locking mechanism 30 contacts or interlocks with the dilator 24. Prior to removing the guidewire 28, the locking mechanism 30 can interlock with the dilator 24 by abutting the wall 58. Accordingly, further withdrawal of the dilator 24 will also withdraw the locking mechanism 30 and the guidewire 28 from the sheath 26.

Figure 19:
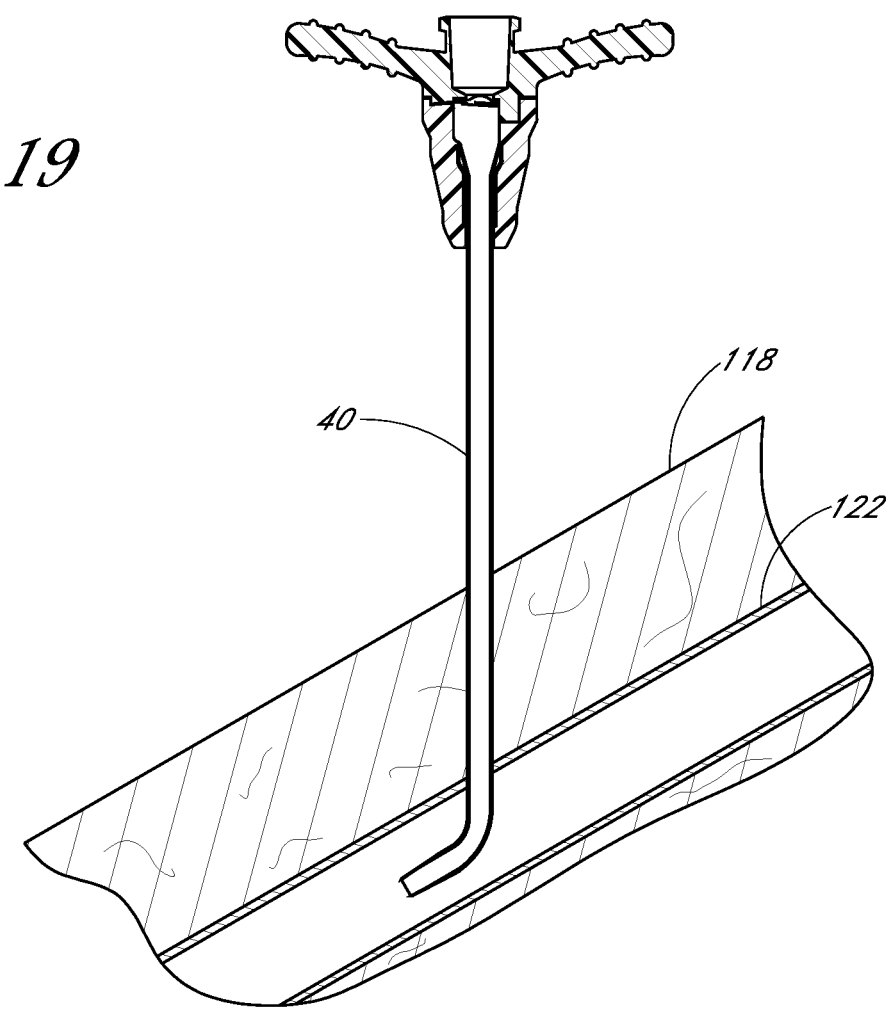
FIG. 19 is a side cross-sectional view of the dilator and the sheath of FIG. 18 where the dilator has been withdrawn from the patient and the sheath.

FIG. 19 is a cross-sectional view similar to FIG. 18 where the dilator 24 has been removed from the patient and the sheath 26. The sheath 26 is left properly inserted within the blood vessel 122. The dilator 24 may be removed after or in concert with removal of the guidewire 28.

Figure 20:
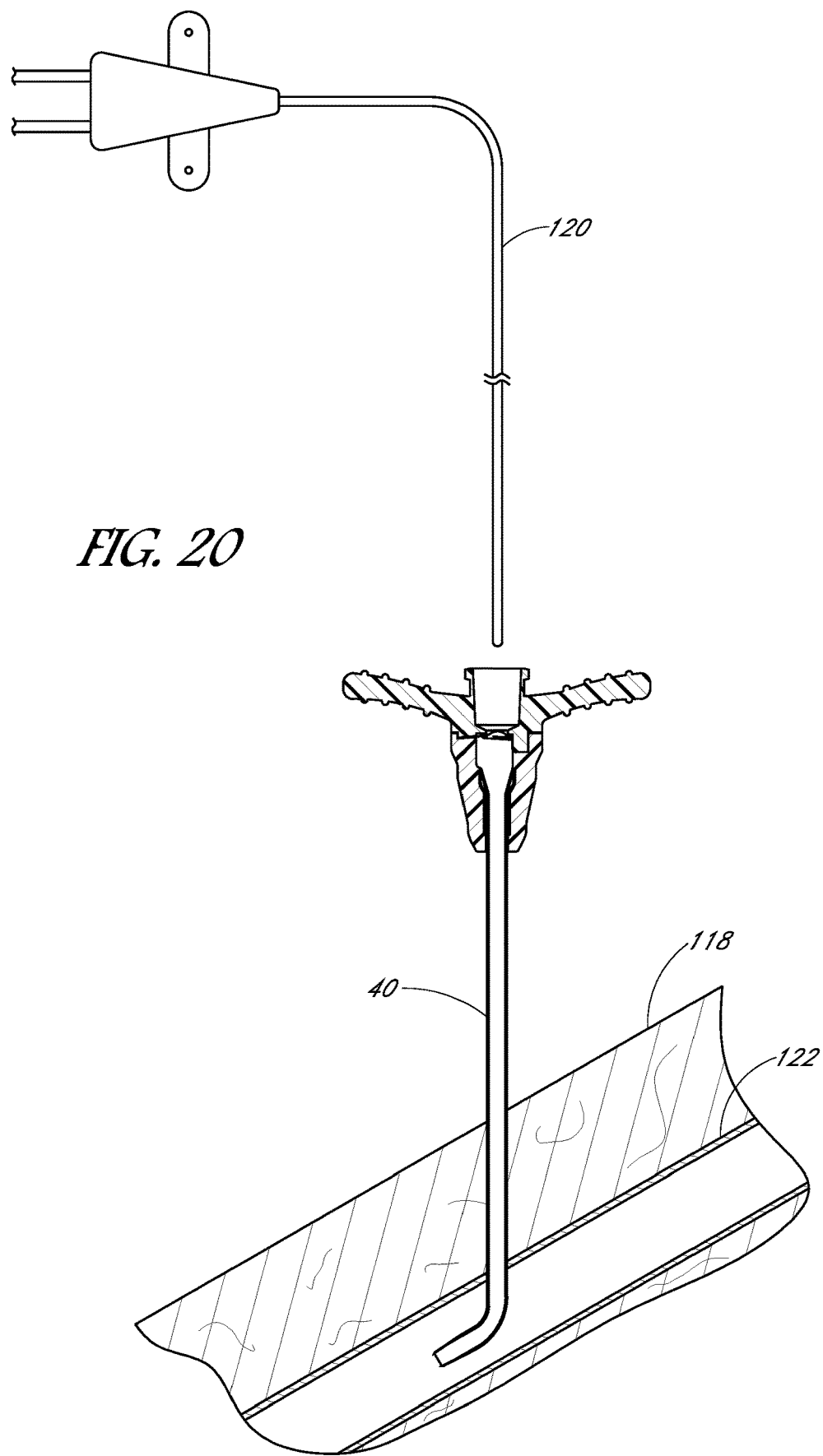
FIG. 20 is a side cross-sectional view of the sheath of FIG. 19 where a catheter is aligned with the sheath for insertion into the patient's vasculature.
Figure 21:
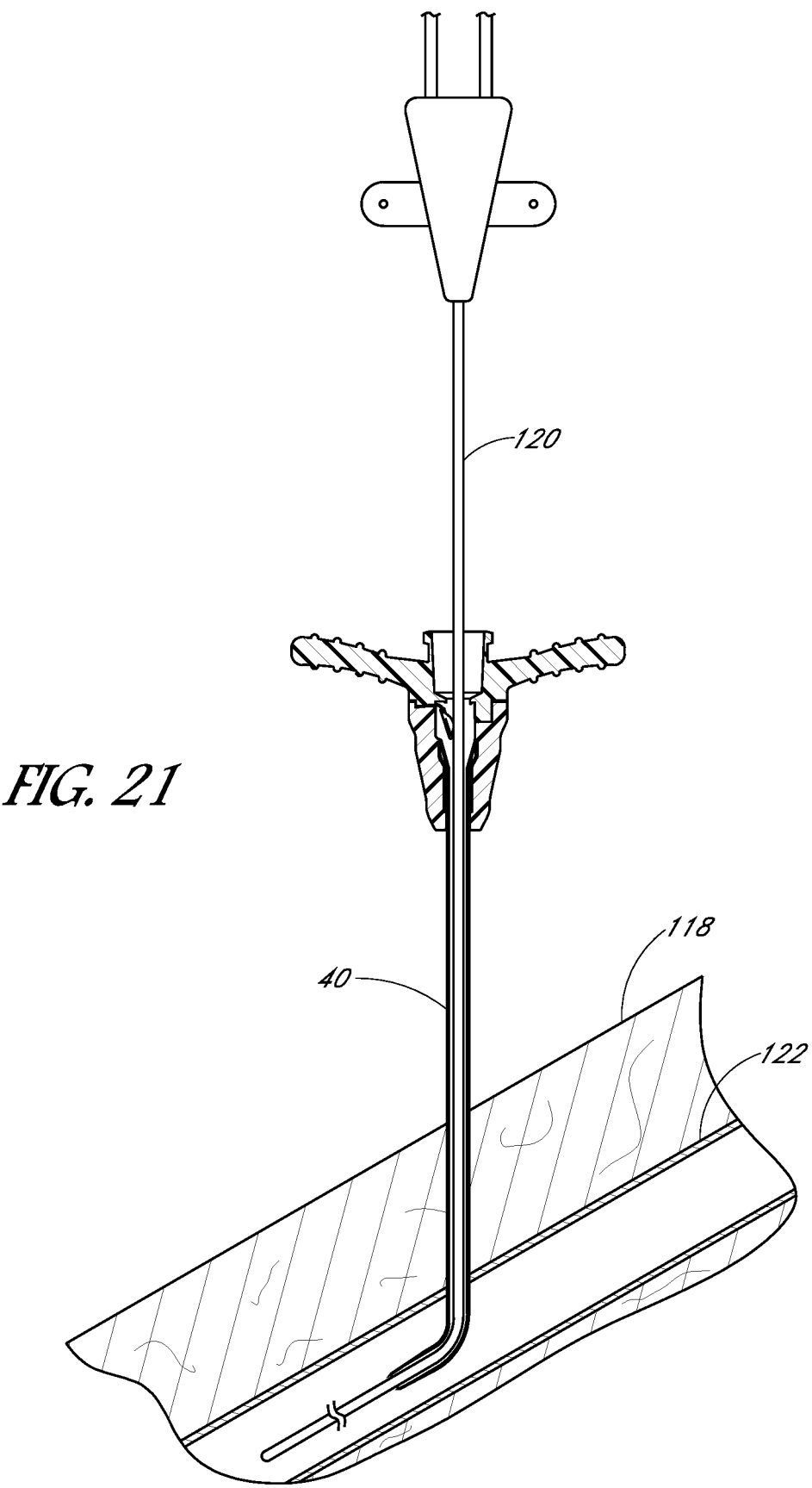
FIG. 21 is a side cross-sectional view of the sheath of FIG. 20 where the catheter has been inserted through the sheath and into the patient's vasculature.

FIG. 20 is a cross-sectional view similar to FIG. 19 where a catheter 120 is aligned with the sheath 26 for insertion into the patient's vasculature. FIG. 21 is a cross-sectional view similar to FIG. 20 where the catheter 120 has been inserted through the sheath 26 and into the patient's vasculature, specifically the targeted blood vessel 122.

Figure 22:
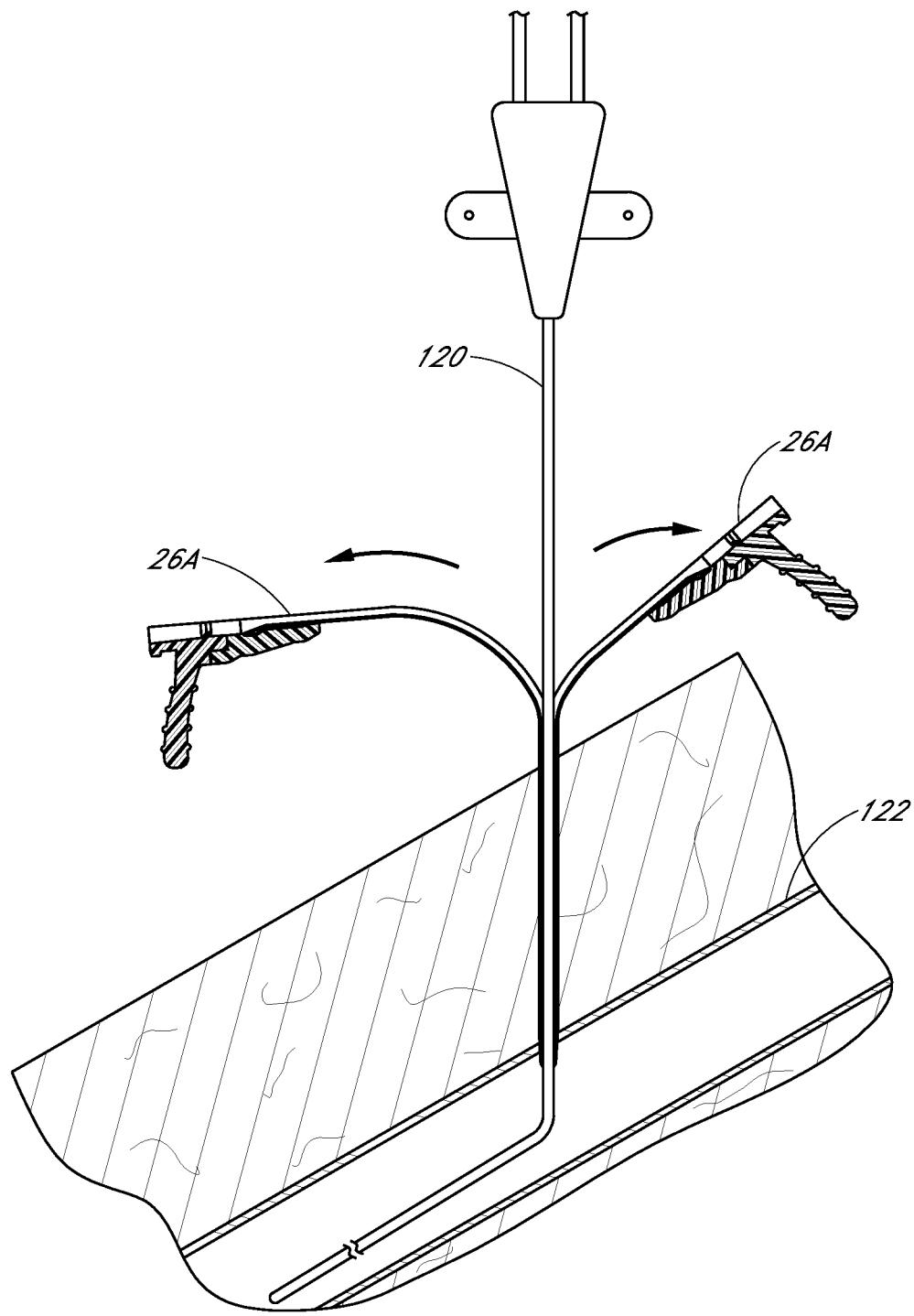
FIG. 22 is a side cross-sectional view of the sheath of FIG. 21 where two portions of the sheath are being peeled away from each other to remove the sheath from encircling the catheter.

FIG. 21 is a cross-sectional view similar to FIG. 20 where two portions of the sheath 26 are being peeled away from each other to remove the sheath 26 from encircling the catheter 120. The sheath 26 is splittable along one or more split lines. A splittable sheath 26 provides the advantage of allowing a portion of or the entire sheath body 40 to be removed depending on the type of catheter or medical article that is to be inserted into the vessel after employing the access device 20. For example, after the catheter 120 is inserted into the blood vessel 122, a portion of the sheath body 40 is separated or peeled-away and removed to reduce clutter at the access site. The peel-away sheath 26 can be first slid in a proximal direction along the catheter 120 until the sheath 26 is removed from the patient and then split apart. Alternatively, the sheath 26 can be initially split prior to the entire sheath 26 being removed from the patient. After the remainder of the sheath 26 is removed from the patient, the physician or healthcare provided can continue splitting the sheath 26. Of course, the sheath 26 could be split in concert with its removal from the patient as is illustrated in FIG. 22. In certain embodiments, the sheath 26 is not splittable.

FIGS. 23A-24B are various views of a locking mechanism to engage the guidewire 28, according to some embodiments. In particular, FIG. 23A is a front view of an embodiment of a locking mechanism 130, and FIGS. 23B and 23C are rear and side cross-sectional views of the locking mechanism 130, respectively. FIGS. 24A and 24B are side cross-sectional views of an embodiment of a method of engaging the locking mechanism 130 with a guidewire 28 including a guidewire stop 92B. Unless otherwise noted, the locking mechanism 130 as shown in FIGS. 23A-24B may include components that are the same as or generally similar to the components in the remaining figures discussed herein, as identified by similar reference numerals. It will be understood that the features described with reference to locking mechanism 130 shown in FIGS. 23A-24B can be used with any of the embodiments described and/or contemplated herein. It will also be understood that any feature, structure, material, step, or component of any embodiment described and/or illustrated herein can be used with or instead of any other feature, structure, material, step, or component of any embodiment of locking mechanism 130 shown in FIGS. 23A-24B.

As shown in the illustrated embodiment, the locking mechanism 130 may comprise a sphere including an external wall 132. The locking mechanism 130, as illustrated, may be hollow in order to receive at least a portion of the guidewire 28 within an internal cavity 134 of the locking mechanism. In some embodiments, the locking mechanism 130 may comprise one or more openings. A user may utilize the one or more openings to permit a guidewire 28 to pass through the locking mechanism 130 and engage a guidewire stop 92B within the internal cavity 134 to prevent unintended removal of the locking mechanism 130 from the guidewire 28. In some embodiments, the locking mechanism 130 can comprise an elastomeric material and/or flexible structure capable of slight deformation as the guidewire stop 92B passes through the one or more openings of the locking mechanism 130.

A first opening may function as a guidewire lock 144, as described herein. A second opening 182 may allow a portion of the guidewire 28 proximal to the guidewire stop 92B to pass through and/or exit the internal cavity 134 of the locking mechanism 130, while still maintaining a portion of the guidewire 28 (e.g., the guidewire stop 92B) within the internal cavity 134. As shown in FIGS. 23C-24B, the openings may be located on opposite sides of the external wall 132.

In some embodiments, the first opening or locking element 144 may be located at a distal end of the locking mechanism 130. The opening of the locking element 144 may not comprise a constant diameter along the entire length of the external wall 132 of the locking mechanism 130 (as shown in FIG. 23C). For example, the locking element 144 may include an external opening 146 and an internal opening 148 of varying diameters that extend through the external wall 132. In some embodiments, a diameter of the external opening 146 of the locking element 144 can be larger than a diameter of the internal opening 148 of the locking element 144. As such, the locking element 144 may taper towards the internal opening 148. The tapering may advantageously permit the guidewire stop 92B to pass through the locking element 144 only in a proximal direction and into the internal cavity 134, while inhibiting the guidewire stop 92B from passing through the locking element 144 in a distal direction once the guidewire stop d92B has been inserted into the internal cavity 144. The locking element 144 can comprise any suitable shape and configuration capable of receiving and/or engaging the guidewire stop 92B. For example, as shown in FIGS. 23C-24B, the locking element 144 can comprise a generally conical shape, although it will be appreciated that the locking element 144 can comprise any suitable wall structure (e.g., straight and/or curved) and have any suitable shape (e.g., cylindrical, tapered).

As illustrated in FIGS. 24A and 24B, the diameter of the external opening 146 may be larger than the guidewire 28 (e.g., including the guidewire stop 92B), but the diameter of the internal opening 148 may be smaller than at least the guidewire stop 92B. In some instances, the diameter of the internal opening 148 can be smaller than the outer width or diameter of the guidewire stop 92B, but sufficiently large so that the external wall 132 defining the internal opening 148 can temporarily resiliently or flexibly increase in size to permit the guidewire stop 92B to pass through the internal opening 148 in a proximal direction and into the internal cavity 134, while inhibiting removal of the guidewire stop 92B in a distal direction from the internal cavity 134 once inserted.

FIG. 24B show that, in some embodiments, both the second opening 182 and the internal opening 148 can each comprise an internal diameter smaller than an external width of an outer surface of the guidewire stop 92B to prevent the unintended removal of the guidewire stop 92B from the internal cavity 134 in a distal and/or proximal direction. Accordingly, the second opening 182 and the internal opening 148 may be sized to permit only portions of the guidewire 28 that are located distal and/or proximal to the guidewire stop 92B to extend outside of the internal cavity 134, while the guidewire stop 92B remains contained inside of the internal cavity 134.

The locking element 144 can comprise any suitable shape and/or configuration capable of permitting the guidewire stop 92B to access the internal cavity 134 of the locking mechanism 130, while resisting removal of the guidewire stop 92B from within the internal cavity 134. The external wall 132 may comprise any material suitable to permit engagement with the guidewire 28 without causing the locking mechanism 130 to tear or irreversibly stretch or otherwise be damaged upon passage of the guidewire stop 92B through the internal opening 148. To prevent accidental disengagement of the locking mechanism 130 from the guidewire stop 92B, in some embodiments, the locking mechanism 130 can comprise a semi-rigid or resilient or elastomeric material capable of slight deformation when a force is applied. As the guidewire stop 92B is inserted into the internal cavity 134, the internal opening 148 can be configured to deform radially outward or in an opening direction that is generally perpendicular to the longitudinal axis of the guidewire stop 92B. In some embodiments, the internal opening 148 can be configured to rebound radially inward in a closing direction, generally opposite from the opening direction, after the guidewire stop 92B is inserted into the internal cavity 134 (as shown in FIG. 24B). This may advantageously allow the internal opening 148 of the locking element 144 to temporarily and/or permanently retain the guidewire stop 92B within the internal cavity 134.

FIGS. 25A-26B are various views of another locking mechanism to engage the guidewire 28, according to some embodiments. In particular, FIG. 25A is a front view of an embodiment of a locking mechanism 230, and FIG. 25B is a side cross-sectional view of the locking mechanism 230. FIGS. 26A and 26B are side cross-sectional views of an embodiment of a method of engaging the locking mechanism 230 with a guidewire 28 including a guidewire stop 92B. Unless otherwise noted, the locking mechanism 230 as shown in FIGS. 25A-26B may include components that are the same as or generally similar to the components in the remaining figures discussed herein, as identified by similar reference numerals. It will be understood that the features described with reference to locking mechanism 230 shown in FIGS. 25A-26B can be used with any of the embodiments described and/or contemplated herein. It will also be understood that any feature, structure, material, step, or component of any embodiment described and/or illustrated herein can be used with or instead of any other feature, structure, material, step, or component of any embodiment of locking mechanism 230 shown in FIGS. 25A-26B.

The locking mechanism 230, as illustrated, can comprise a sheath or disc that is configured to interact with at least a portion of the guidewire 28 (e.g., the guidewire stop 92B), as shown in FIGS. 26A and 26B. The locking mechanism 230, as described herein, can be folded, wrapped, or otherwise positioned over or around the guidewire 28 to enclose at least a portion of the guidewire stop 92B, or otherwise interact with the guidewire stop 92B, to inhibit the locking mechanism 230 and the guidewire stop 92A from moving in a distal direction beyond the dilator hub 38 (e.g., into the dilator shaft).

The locking mechanism 230 can be made of a single unitary body that can fold, be folded, be wrapped, or otherwise automatically position itself over or around, be positioned over or around, or be folded over or around the dilator hub 38 and/or the guidewire 28 to inhibit unintentional distal movement of the guidewire 28 relative to the dilator hub 38. As shown in FIGS. 26A and 26B, respectively, the locking mechanism 230 may have a first configuration positioned on the proximal portion 72 of the dilator hub 38 and a second configuration positioned on and engaged with the guidewire 26.

As illustrated in FIG. 26A, when the locking mechanism is in the first configuration, the locking mechanism 230 may be placed along a proximal portion 72 of the dilator hub 38. The locking mechanism 230 can be sized and configured to extend along and enclose any portion and/or length of the receptacle 74 of the dilator hub 38. For example, the locking mechanism 230 can be configured to be positioned over and enclose the receptacle 74 on a proximal end of the proximal portion 72 of the dilator hub 38. The locking mechanism 230 can be configured such that a first portion 244a of the locking mechanism is positioned along a corresponding first portion of the dilator hub 38, and a second portion 244b of the locking mechanism 230 is positioned along a corresponding second portion of the dilator hub 38 to substantially enclose the receptacle 74. The locking mechanism 230 can be configured to adhere to the dilator hub 32 when positioned. In some embodiments, the first portion 244a and the second portion 244b of the locking mechanism 230 can adhere at least to the dilator hub 38 along an engagement portion comprising an adhesive. In some embodiments, the engagement portion can extend along an entire outer perimeter of the locking mechanism 230.

The locking mechanism 230 can comprise an opening 282 that is sized and configured to selectively permit at least a portion of the guidewire 28 to pass through. An inner diameter of the opening 282, as described herein, can be sufficiently large to permit a portion of the guidewire 28 to reside within and/or pass through the opening 282. However, the inner diameter of the opening 282 is not large enough to permit at least another portion of the guidewire 28 to pass through the opening 282 (e.g., the guidewire stop 92B). As such, the guidewire stop 92B may generally be too large to fit through the opening 282 and further proximal movement of the guidewire 28 relative to the dilator hub 38 will remove the locking mechanism 230 from the dilator hub 38 in a proximal direction to detach the locking mechanism 230 from the dilator hub 38, as described with reference to FIG. 26B.

In some instances, when the locking mechanism 230 is in the second configuration, the locking mechanism 230 can be positioned around the guidewire stop 92B such that the locking mechanism 230 prevents the guidewire stop 92B from moving distally beyond the dilator hub 38. As the guidewire 28 is moved in a proximal direction relative to the dilator hub 38 (shown in FIG. 26A), the guidewire stop 92B can abut against and/or engage the locking mechanism 230. Further distal movement of the guidewire stop 92B relative to the dilator hub 38 can cause the guidewire stop 92B to peel off and/or detach the locking mechanism 230 from the dilator hub 38. Removal of the locking mechanism 30 from the dilator hub 38 may cause the locking mechanism 230 to become folded over the guidewire stop 92B (shown in FIG. 26B). In some instances, the first portion 244a and/or the second portion 244b of the locking mechanism 230, once removed from the dilator hub 38, may adhere to and/or engage the guidewire 28 to enclose at least a portion of the guidewire stop 92B. The locking mechanism 230 can enclose the guidewire stop 92B to inhibit access of the guidewire stop 92B in a distal direction beyond the dilator hub 38, as described herein. The locking mechanism 230 can be folded in the lateral direction and/or the longitudinal direction to cover the guidewire stop 92B.

In some embodiments, the locking mechanism 230, when in the second configuration (as illustrated in FIG. 26B), can be formed by folding, wrapping, enveloping, or crimping the locking mechanism 230 around or over at least a portion of the guidewire 28 to cover at least the guidewire stop 92B. The first portion 244a and/or the second portion 244b can be configured to engage and/or adhere to a portion of the locking mechanism 230 itself and/or any portion of the guidewire 28.

The locking mechanism 230 can be circular (as illustrated), square, rectangular, oval, or any other suitable size and/or shape to enclose and/or form a radial extension from a portion of a guidewire. The locking mechanism 230 can initially be substantially flat for ease of manufacturing and assembly. The locking mechanism 230 can be made of a variety of flexible or semi-rigid materials such as polyester film or sheet, plastic sheet or film, or PET (polyethylene terephthalate). For example, the locking mechanism 230 can comprise Mylar® polyester film. The locking mechanism 230 can be formed by adhering a plastic sheet or film over the dilator hub 38, as described herein.

FIGS. 28A-29B are various views of a locking mechanism to engage the guidewire 28, according to some embodiments. In particular, FIG. 28A is a front view of an embodiment of a locking mechanism 330, and FIGS. 28B and 28C are rear and side cross-sectional views of the locking mechanism 330, respectively. FIGS. 29A and 29B are side cross-sectional views of an embodiment of a method of engaging the locking mechanism 330 with a guidewire 28 including a guidewire stop 92B. Unless otherwise noted, the locking mechanism 330 as shown in FIGS. 28A-29B may include components that are the same as or generally similar to the components in the remaining figures discussed herein, as identified by similar reference numerals. It will be understood that the features described with reference to locking mechanism 330 shown in FIGS. 28A-29B can be used with any of the embodiments described and/or contemplated herein. It will also be understood that any feature, structure, material, step, or component of any embodiment described and/or illustrated herein can be used with or instead of any other feature, structure, material, step, or component of any embodiment of locking mechanism 330 shown in FIGS. 28A-29B.

As shown in the illustrated embodiment, the locking mechanism 330 may comprise a cylinder including an external wall 332. The locking mechanism 330, as illustrated, may be substantially hollow in order to receive at least a portion of the guidewire 28 within an internal cavity 334 of the locking mechanism 330. In some embodiments, the locking mechanism 330 may comprise one or more openings. A user may utilize the one or more openings to permit a guidewire 28 to pass through at least a portion of the locking mechanism 330. A first opening 346 may permit at least a portion of the guidewire 28 to enter the internal cavity 334 of the locking mechanism 330. A second opening 382 may allow a portion of the guidewire 28 proximal to the guidewire stop 92B to pass through and/or exit the internal cavity 334 of the locking mechanism 330, while still maintaining a portion of the guidewire 28 (e.g., the guidewire stop 92B) within the internal cavity 334. As shown in FIGS. 28C-29B, the openings may be located on opposite sides of the external wall 132.

The locking mechanism 330 can comprise a locking element 344 to engage a guidewire stop 92B within the internal cavity 334 and to prevent unintended removal of the locking mechanism 330 from the guidewire 28. In some embodiments, the locking element 344 can comprise an adhesive, elastomeric, and/or gel-like material (e.g., silicone or acrylic gel) capable of interacting and/or interlocking with at least a portion of the guidewire 28 (e.g., the guidewire stop 92B), as shown in FIG. 29B. The locking mechanism 330, as described herein, can adhere, attach, engage, or otherwise interact with (e.g., mold around or envelop) at least a portion of the guidewire stop 92B to inhibit the locking the locking mechanism 330 and the guidewire stop 92B from moving in a distal direction beyond the dilator hub 38 (e.g., into the dilator shaft).

The locking element 344 can be made of a single unitary body that can be positioned within the internal cavity 334 of the locking mechanism 330 to inhibit unintentional distal movement of the guidewire 28 relative to the dilator hub 38. In some embodiments, the locking element 344 may be located at least along a proximal end of the internal cavity 334. As shown in the illustrated embodiment, the locking element 344 may comprise a generally cylindrical shape that may be substantially hollow in order to receive at least a portion of the guidewire 28 within the locking element 344. In some embodiments, the locking element 344 may comprise one or more element openings. A user may utilize the one or more element openings to permit at least a portion of the guidewire 28 to pass through the locking element 344.

In some embodiments, an internal passage defined by an element internal wall 345 extending through the locking element 344. The internal wall 345 of the locking element 144 may not comprise a constant internal diameter along the entire length of the internal wall 345 of the locking element 344 (as shown in FIGS. 28C-29B). For example, the locking element 344 may include a first element opening 346 and a second element opening 348 of varying diameters that are located on opposite ends of the internal wall 345 (e.g., a distal end and a proximal end, respectively). In some embodiments, a diameter of the first element opening 346 of the locking element 344 can be larger than a diameter of the second element opening 348 of the locking element 144. As such, the internal wall 345 may taper towards the smaller diameter of the second element opening 348. The tapering may advantageously facilitate passage of at least a portion of the guidewire 28 through the locking element 344 in a proximal direction, while inhibiting the guidewire stop 92B from passing through the locking element 344 in a distal direction once the guidewire stop 92B has interlocked with the locking element 344, as described herein. For example, the tapering of the internal wall 345 may facilitate guiding (e.g., funneling) a proximal end of the guidewire 28 through the locking mechanism 330.

As illustrated in FIGS. 29A and 29B, the diameter of the first element opening 346 may be larger than the guidewire 28 (e.g., including the guidewire stop 92B), but the diameter of the second element opening 348 may be smaller than at least the guidewire stop 92B. In some instances, the diameter of the second element opening 348 can be smaller than the outer width or diameter of the guidewire stop 92B, such that the internal wall 345 tapering towards the second element opening 348 can engage the guidewire stop 92B as the guidewire stop 92B passes through the locking element 344 (as shown in FIG. 29B).

The second element opening 348 may be comprise a similar sized to the opening 382, such that the second element opening 348 allows a portion of the guidewire 28 proximal to the guidewire stop 92B to pass through and/or exit the internal cavity 334 of the locking mechanism 330, while still maintaining a portion of the guidewire 28 (e.g., the guidewire stop 92B) within the internal cavity 334. The second element opening 348 may be coaxially aligned with the opening 382.

The locking element 344 can comprise any suitable shape and configuration capable of receiving and/or engaging the guidewire stop 92B to inhibit removal of the guidewire stop 92B in a distal direction from the locking element 344 once inserted. For example, as shown in FIGS. 28A-29B, the locking element 344 can comprise a generally cylindrical shape, although it will be appreciated that the locking element 344 can comprise any suitable wall structure (e.g., straight and/or curved) and have any suitable shape (e.g., cylindrical, rectangular, tapered). In some embodiments, the locking element 344 may be configured to temporarily resiliently or flexibly increase in size to permit the guidewire stop 92B to continue to pass through the locking element 344 in a proximal direction once the guidewire wire stop 92B initially engages the locking element 344. The locking element 344, in some instances, can be made of a variety of flexible or semi-rigid materials having adhesive-like properties such as a silicone gel. The locking element 344 can be formed by attaching an adhesive substance within the internal cavity 334 of the locking mechanism 330.

The engaging and/or adhesive force of the locking element 344, in some instances, may not be sufficient to engage with the guidewire 28 as the guidewire 28 is initially passed through the locking element 344. In certain embodiments, the adhesive force of the locking element 344 on the guidewire 28 is insufficient to prevent movement of the guidewire 28 relative to the locking mechanism 330. The adhesive force of the locking element 344 on the guidewire 28 may still permit relatively-free movement (e.g., with minimal resistance) of the guidewire 28 relative to the locking element 344 until the locking element 344 interlocks or engages with the guidewire stop 92B. For example, the locking element 344 may not sufficiently resist passage of the guidewire 28 through the locking element 344 before the locking element 344 engages the guidewire stop 92B. Once the locking element 344 engages with the guidewire stop 92B, the locking element 344 inhibits at least further distal movement of the guidewire 28 relative to the locking element 344.

As illustrated in FIG. 29A, the locking mechanism 330 may be placed within the receptacle 74 of the dilator hub 38. The locking mechanism 330 can be sized and configured to extend along and enclose any portion and/or length of the receptacle 74. The locking mechanism 330 can be configured to be positioned within the dilator hub 32 through any mechanism described herein. The locking mechanism 330 can be removably engaged with at least a portion of the dilator hub 38 so that the locking mechanism 330 can move in or out of the receptacle 74 when the dilator hub 38 is slid in a proximal or distal direction, respectively, along the guidewire 28 once the locking mechanism 330 interlocks with the guidewire 28. For example, the locking mechanism 330 may be removably held within the receptacle 74 via any suitable interaction (e.g., interference, engagement, friction, mechanical coupling, adhesion, etc.). In certain embodiments, once the locking mechanism 330 interlocks with the guidewire 28, the guidewire 28 and locking mechanism 330 move in unison during removal of the guidewire 28. For example, once the locking mechanism 330 interlocks with the guidewire 28, further proximal movement of the guidewire 28 relative to the dilator 24 may be sufficient to overcome the interactive force removably holding the locking mechanism 330 within the receptacle 74.

As described, an inner diameter of the second element opening 348 can be sufficiently large to permit a portion of the guidewire 28 to reside within and/or pass through the second element opening 348. However, the inner diameter of the second element opening 348 is not large enough to permit at least another portion of the guidewire 28 to pass through the second element opening 348 (e.g., the guidewire stop 92B). As such, the guidewire stop 92B may generally be too large to fit through the second element opening 348 and further proximal movement of the guidewire 28 relative to the dilator hub 38 will engage the locking mechanism 330 with at least a portion of the guidewire 28 (e.g., the increased width of the guidewire stop 92B) to interlock the locking mechanism 330 with the guidewire 28, as described with reference to FIG. 29B.

When the guidewire stop 92B engages with the locking mechanism 330, the locking element 344 attaches to the guidewire stop 92B such that the locking mechanism 330 prevents the guidewire stop 92B from moving distally beyond the dilator hub 38. As the guidewire 28 is moved in a proximal direction relative to the dilator hub 38 (shown in FIG. 29A), the guidewire stop 92B can abut against and/or engage the locking element 344. The locking element 344 can engage the guidewire stop 92B to inhibit access of the guidewire stop 92B in a distal direction beyond the dilator hub 38.

The embodiments herein described are comprised of conventional, biocompatible materials. For example, the needle preferably consists of ceramic, a rigid polymer, or a metal such as stainless steel, nitinol, or the like. The other elements can be formed of suitable polymeric materials, such as polycarbonate, nylon, polyethylene, high-density polyethylene, polypropylene, fluoropolymers and copolymers such as perfluoro (ethylene-propylene) copolymer, polyurethane polymers or co-polymers.

As noted above, the present access device can be used to place a catheter at other locations within a patient's body. Thus, for example, but without limitation, the access device can be used as or with a variety of catheters to drain fluids from abscesses, to drain air from a pneumotorax, and to access the peritoneal cavity.

Although this invention has been disclosed in the context of certain preferred embodiments and examples, it will be understood by those skilled in the art that the present invention extends beyond the specifically disclosed embodiments to other alternative embodiments and/or uses of the invention and obvious modifications and equivalents thereof. In addition, while a number of variations of the invention have been shown and described in detail, other modifications, which are within the scope of this invention, will be readily apparent to those of skill in the art based upon this disclosure. It is also contemplated that various combinations or sub-combinations of the specific features and aspects of the embodiments may be made and still fall within the scope of the invention. Accordingly, it should be understood that various features and aspects of the disclosed embodiments can be combined with or substituted for one another in order to form varying modes of the disclosed invention. Thus, it is intended that the scope of the present invention herein disclosed should not be limited by the particular disclosed embodiments described above, but should be determined only by a fair reading of the disclosure and the claims that follow.

What is claimed is:

1. An access device for placing a medical article within a body space, the access device comprising:
    a dilator having a hub and an elongated dilator body extending from the hub;
    a guidewire being configured to slide within the elongated dilator body and having a guidewire stop, the guidewire stop being receivable through the elongated dilator body, the guidewire stop being shaped to enlarge a cross-sectional dimension of the guidewire relative to adjacent sections of the guidewire; and
    a locking mechanism being removably engaged with and being supported by the dilator prior to the dilator being threaded over the guidewire, the locking mechanism comprising:
        a guidewire lock comprising at least one member being disposed within the dilator hub in an initial position to receive a proximal end of the guidewire when the dilator is threaded over the guidewire, the at least one member being movable from the initial position, and
        a portion having an opening extending therethrough, the opening being of a size and shape configured to receive the guidewire and to inhibit the guidewire stop from passing through the opening,
    wherein the locking mechanism is configured to interlock with the guidewire by interaction between the guidewire and at least the one member of the guidewire lock after the one member moves from the initial position as the dilator is threaded over a length of the guidewire,
    wherein a distal end of the guidewire extends distally from a distal end of the dilator when the locking mechanism interlocks with the guidewire,
    wherein the at least one member of the guidewire lock moves to an engaged state from a non-engaged state when in the initial position,
    wherein the at least one member is biased toward the engaged state in which the guidewire lock interacts with the guidewire, and
    wherein the locking mechanism and the dilator are further configured to permit removal of the locking mechanism from the dilator by moving the guidewire axially in a proximal direction relative to the dilator with the guidewire stop abutting at least part of the locking mechanism.

2. The access device of claim 1, wherein the dilator is sized and shaped relative to the locking mechanism so as to inhibit the locking mechanism from passing entirely through the dilator in a distal direction.

3. The access device of claim 2, wherein the dilator includes a receptacle for receiving the locking mechanism, the receptacle including an abutment surface configured to inhibit the locking mechanism from moving in the distal direction relative to the dilator.

4. The access device of claim 1, wherein the guidewire stop is an outward protrusion disposed on the guidewire.

5. The access device of claim 4, wherein the outward protrusion is annular.

6. The access device of claim 1, wherein the guidewire tapers at least along a portion of its length, the portion being located at the guidewire stop.

7. The access device of claim 1, wherein the locking mechanism interlocks with the guidewire at a location on a proximal side of at least a portion of the dilator.

8. The access device of claim 7, wherein the guidewire lock is sized and shaped to allow the guidewire to move through the locking mechanism in a proximal direction relative to the locking mechanism until the guidewire stop contacts at least part of the portion of the locking mechanism that the opening extends through and the guidewire lock interlocks with the guidewire.

9. The access device of claim 1, wherein the at least one member of the guidewire lock comprises one or more tabs configured to interlock with the guidewire.

10. The access device of claim 1, wherein the locking mechanism comprises metal.

11. The access device of claim 1, wherein the locking mechanism comprises plastic.

12. The access device of claim 1, wherein the locking mechanism has an annular shape.

13. The access device of claim 1, wherein a side view of the locking mechanism has a V-shape.

14. The access device of claim 1, further comprising a sheath, the sheath being disposed about the dilator.

15. The access device of claim 1, wherein the locking mechanism is disposed in the hub.

16. The access device of claim 1, wherein the locking mechanism comprises a sheath, wherein the sheath is configured to be positioned on at least a portion of the hub of the dilator prior to the dilator being threaded over the guidewire, and wherein the sheath is further configured to enclose at least a portion of the guidewire stop while the locking mechanism interlocks with the guidewire.

17. The access device of claim 1, wherein the hub of the dilator comprises at least one protrusion configured to removably engage the at least one member of the locking mechanism such that the at least one member is in the non-engaged state prior to removal of the locking mechanism from the dilator.

18. The access device of claim 1, wherein the portion of the locking mechanism having the opening is chamfered to facilitate passage of the guidewire through the opening.

19. An access device for placing a medical article within a body space, the access device comprising:
a guidewire having a guidewire stop, the guidewire stop being shaped to enlarge a cross-sectional dimension of the guidewire relative to adjacent sections of the guidewire;
a dilator configured to be coaxially disposed about the guidewire; and
a locking mechanism being removably engaged with and disposed on the dilator prior to the dilator being coaxially disposed about the guidewire, the locking mechanism comprising a portion having an opening being of a size and shape configured to receive the guidewire and to inhibit the guidewire stop from passing through the opening, the locking mechanism being configured to move from an unlocked state to a locked state, the locking mechanism being disengaged from the guidewire when the locking mechanism is in the unlocked state so as to receive a proximal end of the guidewire through the locking mechanism and allow axial movement by the guidewire through the locking mechanism in a proximal direction and a distal direction relative to the dilator when the dilator is coaxially disposed over the guidewire, the locking mechanism being engaged with the guidewire when the locking mechanism is in the locked state so as to limit at least axial movement of a portion of the guidewire in the distal direction relative to at least a portion of the dilator,
wherein a distal end of the guidewire extends distally from a distal end of the dilator when the locking mechanism is in the locked state, and
wherein the locking mechanism and the dilator are further configured to permit removal of the locking mechanism from the dilator by moving the guidewire axially in a proximal direction relative to the dilator with the guidewire stop abutting at least part of the portion of the locking mechanism that the opening extends through.

20. The access device of claim 19, wherein the at least axial movement of the portion of the guidewire in the distal direction is inhibited by contact between the locking mechanism and the dilator.

21. The access device of claim 19, wherein the guidewire stop is receivable through the dilator.

22. The access device of claim 19, wherein the dilator is sized and shaped relative to the locking mechanism so as to inhibit the locking mechanism from passing entirely through the dilator in a distal direction.

23. The access device of claim 19, wherein the guidewire stop is an outward protrusion disposed on the guidewire.

24. The access device of claim 19, wherein the locking mechanism engages with the guidewire at a location on a proximal side of at least a portion of the dilator.

25. The access device of claim 19, wherein the locking mechanism comprises a guidewire lock configured to engage the guidewire.

26. The access device of claim 25, wherein the locking mechanism is configured to interlock with the guidewire by engagement between the guidewire lock and the guidewire at least when the dilator is threaded over the guidewire, and wherein the guidewire lock has at least one member being moveable between the locked state and the unlocked state and is biased toward the locked state in which the guidewire lock engages with the guidewire.

27. The access device of claim 19, wherein the locking mechanism has an annular shape.

28. The access device of claim 19, wherein a side view of the locking mechanism has a V-shape.

29. The access device of claim 19, wherein the locking mechanism comprises a sheath, wherein the sheath is configured to be positioned on at least a portion of a hub of the dilator when the locking mechanism is in the unlocked state, and wherein the sheath is further configured to enclose at least a portion of the guidewire stop when the locking mechanism is in the locked state.

30. The access device of claim 19, wherein the locking mechanism comprises:
an external wall defining an internal cavity, the internal cavity being configured to receive at least a portion of the guidewire; and
a locking element configured to be at least partially positioned within the internal cavity,
wherein the locking mechanism is configured to be positioned within a hub of the dilator when the locking mechanism is in the unlocked state, and wherein the locking element is further configured to engage at least a portion of the guidewire stop when the locking mechanism is in the locked state.

* * * * *